(12) United States Patent
Reddy et al.

(10) Patent No.: US 8,907,132 B2
(45) Date of Patent: Dec. 9, 2014

(54) PROCESS FOR PREPARING (R)-2-ACETAMIDO-N-BENZYL-3-METHOXY-PROPIONAMIDE

(75) Inventors: Manne Satyanarayana Reddy, Hyderabad (IN); Sajja Eswaraiah, Hyderabad (IN); Aluru Srinivas, Medak (IN); Revu Satyanarayana, East Godavari (IN)

(73) Assignee: MSN Laboratories Private Limited, Medak District, Telangana (IN)

( * ) Notice: Subject to any disclaimer, the term of this patent is extended or adjusted under 35 U.S.C. 154(b) by 135 days.

(21) Appl. No.: 13/577,804

(22) PCT Filed: Feb. 9, 2011

(86) PCT No.: PCT/IN2011/000087
§ 371 (c)(1),
(2), (4) Date: Oct. 19, 2012

(87) PCT Pub. No.: WO2011/099033
PCT Pub. Date: Aug. 18, 2011

(65) Prior Publication Data
US 2013/0041180 A1    Feb. 14, 2013

(30) Foreign Application Priority Data

Feb. 9, 2010    (IN) .............................. 317/CHE/2010
Feb. 23, 2010   (IN) .............................. 464/CHE/2010
Sep. 6, 2010    (IN) ............................. 2576/CHE/2010
Dec. 15, 2010   (IN) ............................. 3837/CHE/2010

(51) Int. Cl.
| C07C 233/05 | (2006.01) |
| C07C 231/12 | (2006.01) |
| C07C 231/14 | (2006.01) |
| C07C 237/06 | (2006.01) |
| C07C 271/22 | (2006.01) |
| C07C 237/32 | (2006.01) |

(52) U.S. Cl.
CPC ............. *C07C 237/32* (2013.01); *C07C 237/06* (2013.01); *C07C 271/22* (2013.01)
USPC ............................ 564/158; 564/139; 564/144

(58) Field of Classification Search
CPC .... C07C 231/12; C07C 231/14; C07C 233/05
USPC .......................................... 564/139, 144, 158
See application file for complete search history.

(56) References Cited

U.S. PATENT DOCUMENTS

| 5,773,475 A | 6/1998 | Kohn |
| 6,048,899 A | 4/2000 | Kohn et al. |
| 8,598,386 B2 * | 12/2013 | Wisdom et al. ............... 564/158 |
| 2008/0027137 A1 | 1/2008 | Riedner et al. |
| 2009/0143472 A1 | 6/2009 | Madhra et al. |

FOREIGN PATENT DOCUMENTS

| EP | 1 038 522 A2 | 9/2000 |
| WO | WO 9733861 * | 9/1997 |
| WO | WO 2006/037574 A1 | 4/2006 |
| WO | WO 2011/039781 A1 | 4/2011 |

OTHER PUBLICATIONS

Notification Concerning Transmittal of International Preliminary Report on Patentability for International Application No. PCT/IN2011/000087: "Process for Preparing (R)-2-Acetamido-N-Benzyl-3-Methoxy-Propionamide"; Date of Mailing: Aug. 23, 2012.
Written Opinion of the International Searching Authority for International Application No. PCT/IN2011/000087: "Process for Preparing (R)-2-Acetamido-N-Benzyl-3-Methoxy-Propionamide", Date of Mailing: Jul. 14, 2011.
International Search Report from counterpart International Application No. PCT/IN2011/000087, titled "Process for Preparing (R)-2-Acetamido-N-Benzyl-3-Methoxy-Propionamide", dated Jul. 14, 2011.
Andurkar, S., et al., "Synthesis and anticonvulsant activities of (*R*)-(*O*)-methylserine derivatives", *Tetrahedron: Asymmetry*, 9: 3841-3854 (Sep. 1998).
Choi, D., et al., "Synthesis and Anticonvulsant Activities of *N*-Benzyl-2-acetamidopropionamide Derivatives", *J. Med. Chem.* 39: 1907-1916 (1996).

* cited by examiner

*Primary Examiner* — Shailendra Kumar
(74) *Attorney, Agent, or Firm* — Hamilton, Brook, Smith & Reynolds, P.C.

(57) ABSTRACT

Processes for preparing and purifying (R)-2-acetamido-N-benzyl-3-methoxy-propionamide of formula-1 and intermediates thereof are provided.

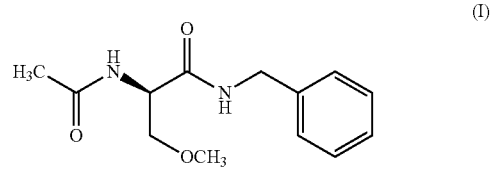

8 Claims, 3 Drawing Sheets

PROCESS FOR PREPARING (R)-2-ACETAMIDO-N-BENZYL-3-METHOXY-PROPIONAMIDE

RELATED APPLICATION

This application is the U.S. National Stage of International Application No. PCT/IN2011/000087, filed Feb. 9, 2011, which designates the U.S., published in English, and claims priority under 35 U.S.C. §§119 or 365(c) to Indian Application No. 317/CHE/2010, filed Feb. 9, 2010, Indian Application No. 464/CHE/2010, filed Feb. 23, 2010, Indian Application No. 2576/CHE/2010 filed Sep. 6, 2010 and Indian Application No. 3837/CHE/2010 filed Dec. 15, 2010. The entire teachings of the above applications are incorporated herein by reference.

FIELD OF THE INVENTION

The present invention relates to novel and improved process for the preparation of (R)-2-acetamido-N-benzyl-3-methoxypropionamide. (R)-2-acetamido-N-benzyl-3-methoxypropionamide is commonly known as "Lacosamide" represented by the following structural formula-1

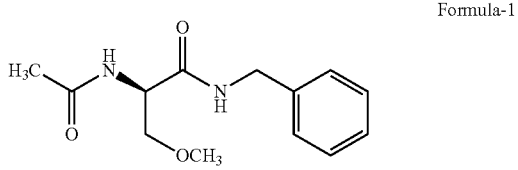 [SMILES: COC[C@@H](NC(C)=O)C(=O)NCc1ccccc1]

Formula-1

Lacosamide is an anticonvulsant drug useful in the treatment of central nervous system disorders such as epilepsy and also useful in the treatment of pain, particularly neuropathic pain such as diabetic neuropathic pain. Lacosamide is marketed under brand name Vimpat®.

BACKGROUND OF THE INVENTION

Lacosamide and process for its preparation was first disclosed in U.S. Pat. No. 5,773,475. Different routes of synthesis for the preparation of Lacosamide have been reported in literature like U.S. Pat. No. 6,048,899, US 2008/027137 and US 2009/143472 and Tetrahedron Asymmetry 1998, 9, 3841-3854.

Lacosamide and process for its preparation was first disclosed in U.S. Pat. No. 5,773,475. The disclosed process involves O-methylation of (R)-2-acetamido-N-benzyl-3-hydroxy propanamide by reacting it with methyl iodide in presence of silver oxide in acetonitrile. The said process involves the usage of costly reagent like silver oxide and methyl iodide for O-methylation increases the cost of production and hence usage of the same in commercial scale is not possible. Moreover lacosamide obtained by the said process contaminated with more impurities. Hence there is a need in the art for the cost effective process preparation of pure lacosamide which involves the usage of simple and cost effective reagent.

Another process was disclosed in Tetrahedron Asymmetry 1998, 9; 3841-3854. The disclosed process involves the reaction of D-Serine with Benzylchloroformate and MgO in diethyl ether to provide (R)—N-(benzyloxycarbonyl)serine, which on further treatment with benzylamine in presence of 4-methylmorpholine and isobutyl chloroformate in THF provides (R)—N-benzyl-2-N(BenzyloXycarbonyl)amino-3-hydroxypropionamide. Thus obtained hydroxy intermediate was methylated by treating with methyl iodide in presence of silver oxide in acetonitrile to provide (R)—N-benzyl-2-N-(Benzyloxycarbonyl)amino-3-methoxypropionamide. Deprotection of the N-protecting group from the obtained methoxy derivative by hydrogenation in presence Pd/C catalyst in methanol provides (R)—N-benzyl-2-amino-3-propionamide, which on Acetylation with acetic anhydride in presence of DMAP and pyridine in THF gives Lacosamide.

The said process has number of disadvantages and hence is difficult to carry out in commercial scale. 1) It involves the usage of MgO and ether solvent for the N-protection of D-serine. The usage of ether solvent and MgO at commercial level is not recommendable. 2) It involves the usage of costly reagent like silver oxide and methyl iodide for O-methylation increases the cost of production and hence usage of the same in commercial scale is not possible. 3) Further it involves the usage of hydrogenation in presence of Pd/C catalyst for deprotection of N-protecting group to get lacosarriide. The usage of Pd/C in commercial level is difficult to handle in safety aspect and increase the cost of production. Hence there is a need in the art for an improved process for the preparation of lacosamide which avoids all the problems mention here.

Later US patent publication US 2008/0027137 disclosed a process for the preparation of (R)-2-((t-butoxy)carbonylamino)-3-methoxypropanoic acid and its conversion to lacosamide. The disclosed process involves the protection of D-serine with di-t-butyl dicarbonate to provide N-Boc-D-serine, which is further O-methylated using dimethylsulphate to provide (R)-2-((t-butoxy)carbonylamino)-3-methoxy propanoic acid. Both the protection and O-methylation reaction were carried in a biphasic solvent system such as in a mixture of toluene & water, in presence of phase transfer catalyst and a base. Even though the disclosed process provides good yield, it involves the usage of costly reagent such as phase transfer catalyst, which increases the cost of production.

It has now surprisingly found by the present inventors that both the protection and O-methylation reaction has been carried out in a single phase solvent system without using costly phase transfer catalyst with good yields and purity, there by reduces the cost of production. The present invention provides an improved process for the preparation of lacosamide, wherein the O-methylation of N-Boc-D-serine and protection of D-serine with di-t-butyl dicarbonate were carried out in a single phase solvent system without usage of phase transfer catalyst.

The main aspect of the present invention is to provide a cost effective process for the preparation of lacosamide which avoids the problems associated with the prior art processes.

BRIEF DESCRIPTION OF THE INVENTION

The first aspect of the present invention is to provide an improved process for the preparation of lacosamide compound of formula-1, which comprises of O-methylating the (R)-2-acetamido-N-benzyl-3-hydroxypropanamide compound of formula-2 with suitable methylating agent in presence of a suitable aqueous base in a suitable solvent and in presence of a phase transfer catalyst provides the lacosamide compound of formula-1.

The second aspect of the present invention is to provide an improved process for the preparation of lacosamide compound of formula-1, which comprises of O-methylating the (R)-2-acetamido-N-benzyl-3-hydroxypropanamide compound of formula-2 with suitable methylating agent in presence of a suitable base in a suitable solvent and in absence of a phase transfer catalyst provides the lacosamide compound of formula-1.

The third aspect of the present invention is to provide an improved process for the preparation of (R)-2-acetamido-N-benzyl-3-hydroxypropanamide compound of formula-2, which comprises of the following steps;
a) Reacting the (R)-2-amino-3-hydroxypropanoic acid compound of formula-3 with acetic anhydride in presence of a suitable solvent provides (R)-2-acetamido-3-hydroxypropanoic acid compound of formula-4,
b) reacting the compound of formula-4 with benzylamine in presence of a base and activator in a suitable solvent provides the compound of formula-2.

The fourth aspect of the present invention is to provide a process for the purification of (R)-2-acetamido-N-benzyl-3-hydroxypropanamide compound of formula-2.

The fifth aspect of the present invention is to provide a process for the purification of lacosamide compound of formula-1.

The sixth aspect of the present invention is to provide a novel process for the preparation of lacosamide compound of formula-1, which comprises of the following steps;
a) Treating the (R)-2-amino-3-hydroxypropanoic acid compound of formula-3 with isobutyl chloroformate in presence of a base in a suitable solvent provides (R)-3-hydroxy-2-(isobutoxycarbonylamino) propanoic acid compound of formula-5,
b) O-methylating the compound of formula-5 with suitable methylating agent in presence of a base or its aqueous solution in a suitable solvent and in presence or absence of phase transfer catalyst, provides the (R)-2-(isobutoxycarbonylamino)-3-methoxypropanoic acid compound of formula-6,
c) reacting the compound of formula-6 with benzylamine in presence of a base and activator in a suitable solvent provides the (R)-isobutyl 1-(benzylamino)-3-methoxy-1-oxopropan-2-ylcarbamate compound of formula-7,
d) treating the compound of formula-7 with suitable acid in suitable solvent provides the (R)-2-amino-N-benzyl-3-methoxypropanamide compound of formula-8,
e) reacting the compound of formula-8 with acetic anhydride in a suitable solvent provides lacosamide compound of formula-1.

The seventh aspect of the present invention is to provide an improved process for the preparation of lacosamide compound of formula-1, which comprises of the following steps;
a) Esterifying the (R)-2-amino-3-hydroxypropanoic acid compound of formula-3 in presence of dry HCl in a suitable alcoholic solvent provides the (R)-alkyl-2-amino-3-hydroxypropanoate hydrochloride compound of formula-9,
b) reacting the compound of formula-9 with benzylamine in a suitable solvent provides (R)-2-amino-N-benzyl-3-hydroxypropanamide compound of formula-10,
c) reacting the compound of formula-10 with acetic anhydride in a suitable solvent provides the (R)-2-acetamido-N-benzyl-3-hydroxypropanamide compound of formula-2,
d) O-methylating the compound of formula-2 with suitable methylating agent in presence of a base or its aqueous solution in a suitable solvent and in presence or absence of phase transfer catalyst provides lacosamide compound of formula-1.

The eighth aspect of the present invention is to provide an improved process for the preparation of lacosamide compound of formula-1, which comprises of the following steps;
a) Reacting the (R)-2-amino-3-hydroxypropanoic acid compound of formula-3 with acetic anhydride in a suitable solvent provides the (R)-2-acetamido-3-hydroxypropanoic acid compound of formula-4,
b) O-methylating the compound of formula-4 with suitable methylating agent in presence of a base or its aqueous solution in a suitable solvent and in presence or absence of phase transfer catalyst provides (R)-2-acetamido-3-methoxypropanoic acid compound of formula-11,
c) reacting the compound of formula-11 with benzylamine in presence of a base and activator in a suitable solvent provides lacosamide compound of formula-1.

The ninth aspect of the present invention is to provide a process for the selective methylation of (R)-2-amino-3-hydroxypropanoic acid compound of formula-3 without protecting amine functional group, which comprises of treating the compound of formula-3 with a suitable methylating agent in presence of a base in a suitable solvent and in presence or absence of a phase transfer catalyst to provide the (R)-2-amino-3-methoxypropanoic acid compound of formula-12.

The tenth aspect of the present invention is to provide to an improved process for the preparation of (R)—N-benzyl-2-amino-3-methoxypropionamide compound of formula-8, which comprises of deprotection of N-protecting group from (R)—N-benzyl-2-N-(benzyloxycarbonypamino-3-methoxypropionamide compound of formula-15 to provide the compound of formula-8, characterized in that the deprotection is carried out in presence of suitable acid.

The eleventh aspect of the present invention is to provide an improved process for the preparation of (R)—N-benzyl-2-N-(benzyloxycarbonyl)amino-3-methoxy propionamide compound of formula-15, which comprises of reacting (R)—N-benzyl-2-N-(benzyloxycarbonypamino-3-hydroxypropionamide compound of formula-14 with a suitable methylating agent in a suitable solvent and in presence or absence of phase transfer catalyst.

The twelfth aspect of the present invention is to provide an improved process fore, the preparation of lacosamide compound of formula-1, which comprises of the following steps,
a) Reacting the D-serine compound of formula-3 with benzylchloroforrnate in a suitable inorganic base in a suitable solvent to provide the (R)—N-(benzyloxycarbonyl)serine compound of formula-13,
b) reacting the compound of formula-13 with benzylamine in presence of isobutylchlorofonnate and N-methyl morpholine in a suitable solvent to provide the (R)—N-benzyl-2-N-(benzyloxycarbonyl)amino-3-hydroxypropionamide compound of formula-14,
c) methylating the compound of formula-14 by treating with a suitable methylating agent in a suitable solvent and in presence or absence of phase transfer catalyst provides (R)—N-benzyl-2-N-(benzyloxycarbonyl)amino-3-methoxypropionamide compound of formula-15,
d) treating the compound of formula-15 with a suitable acid in presence or absence of a solvent to provide the (R)—N-benzyl-2-amino-3-methoxypropionamide compound of formula-8,
e) reacting the compound of formula-8 with acetic anhydride in a suitable inorganic base in a suitable solvent to provide the lacosamide compound of formula-1,
f) optionally purifying the lacosamide using a suitable solvent gives highly pure lacosamide compound of formula-1.

The thirteenth aspect of the present invention is to provide one pot process for the preparation of lacosamide compound of formula-1, which comprises of reacting the (R)—N-benzyl-2-N-(benzyloxycarbonyl)amino-3-methoxypropionamide compound of formula-15 with a suitable acid in presence or absence of a solvent to provide the (R)—N-benzyl-2-amino-3-methoxypropionamide compound of formula-8, which on in-situ reaction with acetic anhydride in a suitable solvent to provide the lacosamide compound of formula-1.

The fourteenth aspect of the present invention provides an improved process for the preparation of (R)-2-(t-butoxycarbonylamino)-3-methoxypropanoic acid compound of formula-17, which comprises of O-methylating the (R)-2-(tert-butyloxycarbonylamino)-3-hydroxypropanoic acid (herein after referred as "N-Boc-D-serine") compound of formula-16 with a suitable methylating agent in the presence of base in a single phase solvent system without usage of a phase transfer catalyst.

The fifteenth aspect of the present invention provides an improved process for the preparation of N-Boc-D-serine compound of formula-16, which comprises of reacting the D-serine with suitable N-protecting reagent in the presence of a base in a single phase system without the usage of phase transfer catalyst.

The sixteenth aspect of the present invention provides an one-pot process for the preparation of lacosamide compound of formula-1 starting from D-serine, where in the protection of D-serine with suitable protecting agent and O-methylation of N-Boc-D-serine was carried out in a single phase system without usage of a phase transfer catalyst.

The seventeenth aspect of the present invention provides novel acid addition salts of (R)—N-benzyl-2-amino-3-methoxypropionamide compound of formula-19, process for its preparation and their use in the synthesis of highly pure compound of formula-8 and lacosamide.

DETAILED DESCRIPTION OF THE INVENTION

Figure 1:
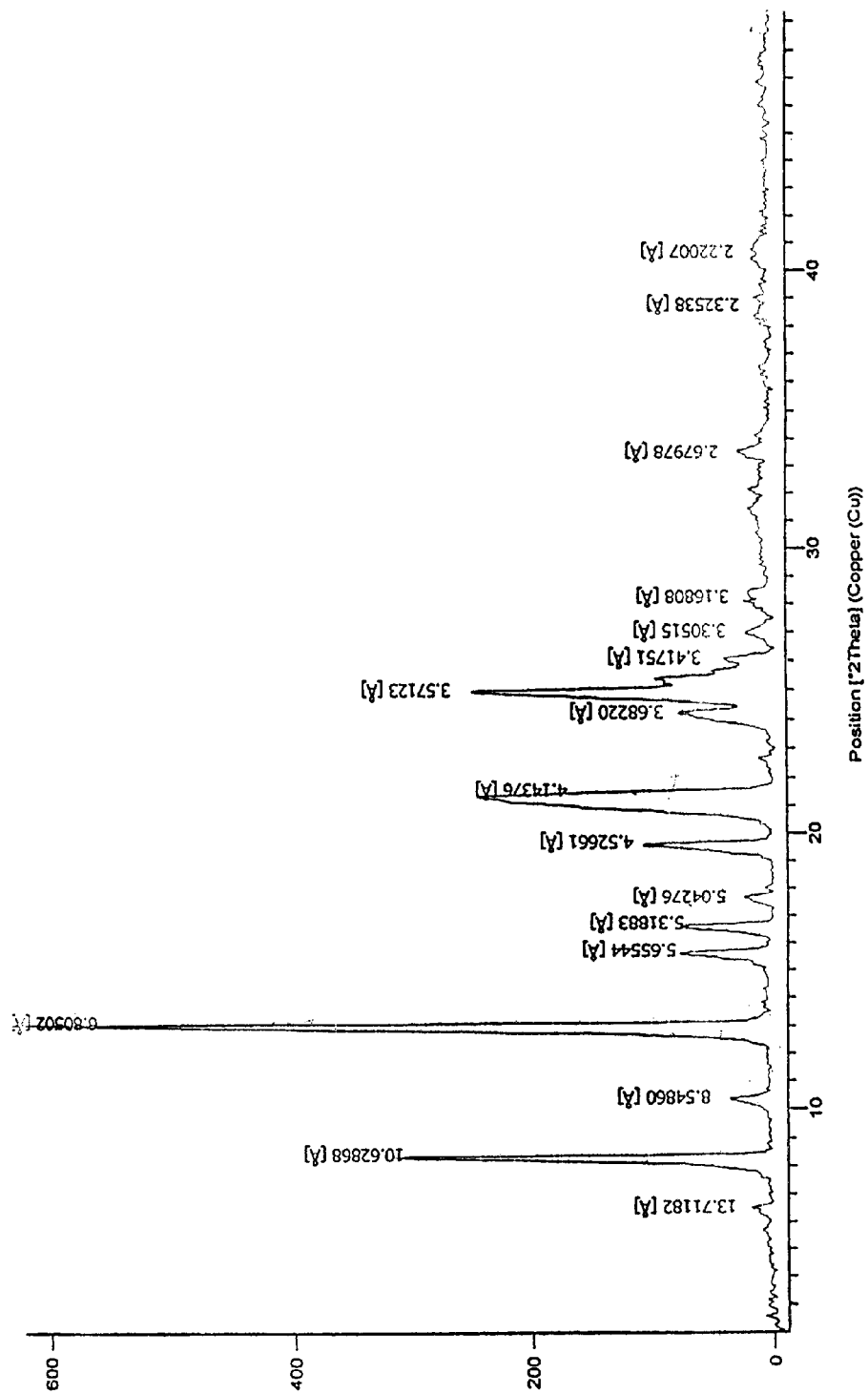
FIG. 1: Illustrates the Powder X-ray diffractogram of lacosamide prepared as per the process disclosed in example-2(b) of U.S. Pat. No. 5,773,475
Figure 2:
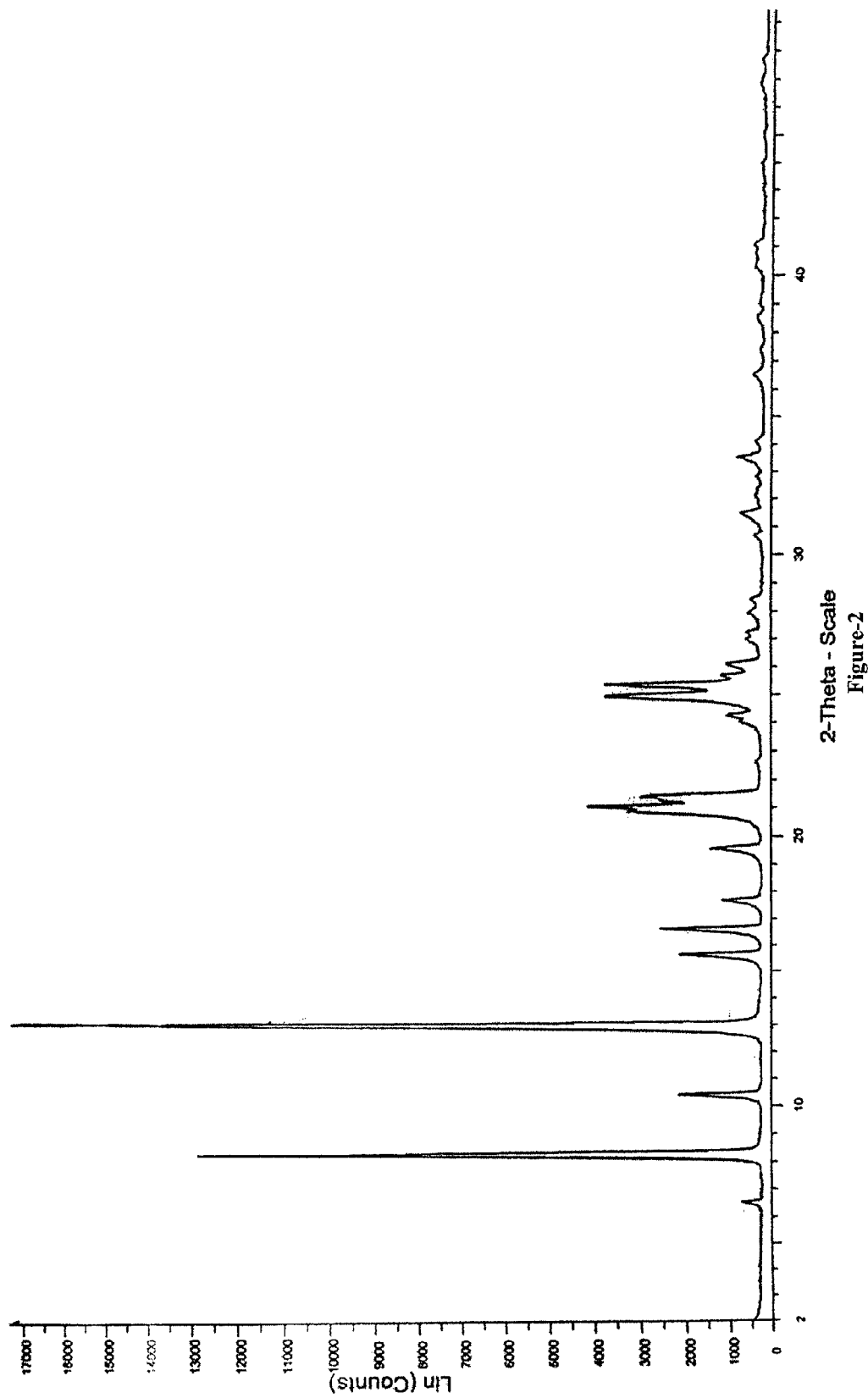
FIG. 2: PXRD pattern of lacosamide prepared as per example-34.
Figure 3:
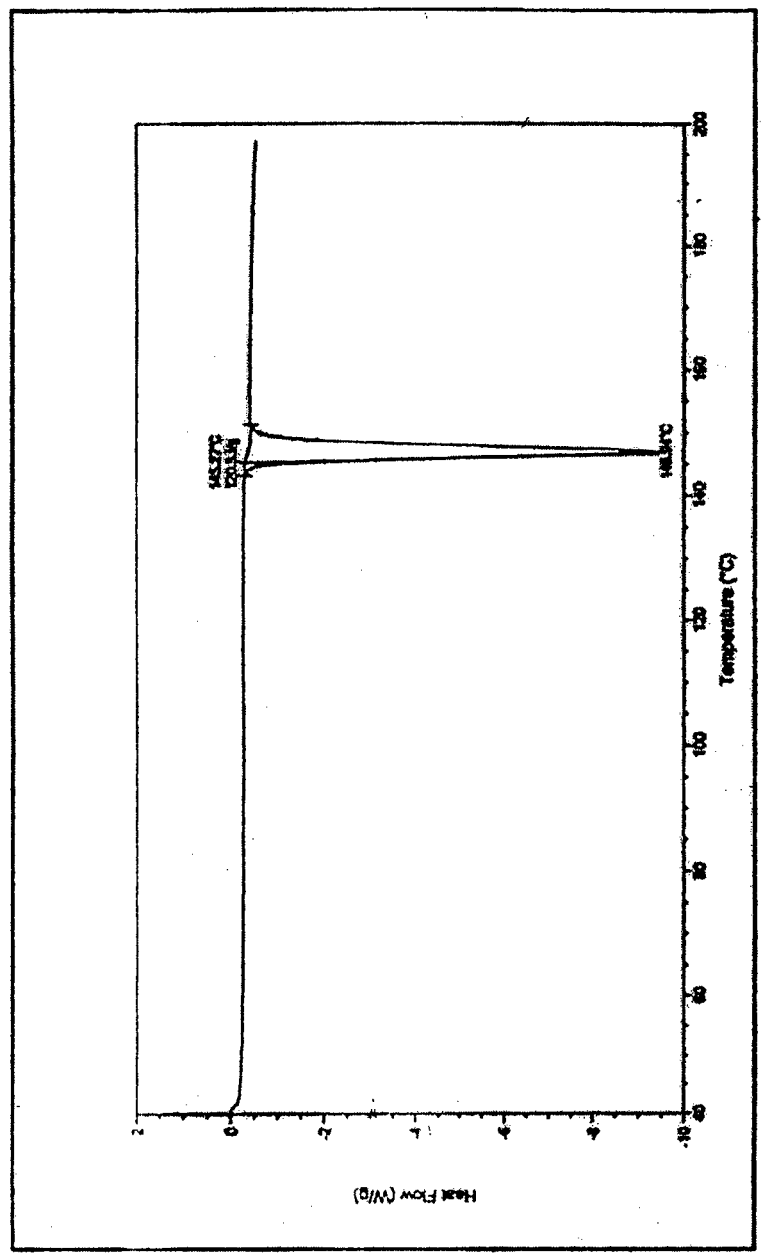
FIG. 3: DSC thermo gram of lacosamide prepared as per example-34.

As used herein the present invention, the term "suitable solvent" refers to the solvent selected from "polar solvents" such as water; "polar aprotic solvents" such as dimethylsulfoxide, dimethylacetamide, dimethyl formamide and the like; "nitrile solvents" such as acetonitrile, propionitrile, butyronitrile and isobutyronitrile and the like; "ether solvents" such as di-tert-butylether, diethylether, diisopropyl ether, 1,4-dioxane, methyltert-butylether, ethyl tert-butyl ether, tetrahydrofuran and dimethoxyethane; "alcohol solvents" such as methanol, ethanol, n-propanol, isopropanol, n-butanol and t-butanol and the like; "chloro solvents" such as methylene chloride, ethylene dichloride, carbon tetra chloride, chloroform, chloro benzene and the like; "hydrocarbon solvents" such as benzene, toluene, xylene, heptane, hexane and cyclohexane; "ketone solvents" such as acetone, ethyl methyl ketone, diethyl ketone, methyl tert-butyl ketone, isopropyl ketone and the like; "esters solvents" such as ethyl acetate, methyl acetate, n-butyl acetate, isobutyl acetate, sec-butyl acetate, isopropyl acetate and the like; and their mixtures thereof.

As used herein the present invention, the term "phase transfer catalyst" refers to the phase transfer catalyst selected from tetraethylammonium p-toluenesulfonate, tetrapropyl ammonium trifluoromethanesulfonate, tetraphenyl phosphonium hexafluoroantimonate, cetylpyridinium bromide, triphenylmethyl triphenyl phosponium chloride, benzyltriethyl ammonium chloride, benzyltrimethylammonium chloride, benzyltriphenylphosphonium chloride, benzytributylammonium chloride, butyl triethylammonium bromide, butyltriphenylphosphonium bromide, cetyltrimethyl ammonium bromide, cetyltrimethyl ammonium chloride, ethyltriphenylphosphonium bromide, ethyltriphenylphosphonium iodide, methyltrioctylammonium bromide, methyltriphenylphosphonium bromide, methyl triphenylphosphonium iodide, phenyl trimethylammonium chloride, tetrabutylammonium hydroxide, tetra butyl ammonium perchlorate, tetrabutylammonium bromide, tetra butyl ammonium hydrogensulphate, tetrabutylammonium iodide, tetrabutylammonium tetra fluoroborate, tetra butyl ammonium thiocyanate, tetraethylammonium hydroxide, tetraethylammonium iodide, tetraethylammonium bromide, tetramethylammonium chloride, tetramethylammonium iodide, tetramethylammonium chloride, tetraoctyl ammonium bromide, tetraphenyl phosphonium bromide, tetrapropylammonium hydroxide, tetrapropylammonium bromide and tributylmethylammonium chloride, tributyl benzyl ammonium bromide, benzyl trimethyl ammonium chloride, tetra butyl ammonium acetate or alkali iodides like sodium iodide, potassium iodide and lithium iodide.

As used herein the term "inorganic base" refers to base selected from alkali metal hydroxides such as sodium hydroxide, potassium hydroxide, lithium hydroxide; alkali metal carbonates such as sodium carbonate, potassium carbonate, cesium carbonate and lithium carbonate; Alkali metal bicarbonates such as sodium bicarbonate and potassium bicarbonate; alkali metal alkoxides such as sodium methoxide, potassium methoxide, sodium tertiary butoxide, potassium tertiary butoxide or mixtures thereof;

As used herein the term "organic base" refers to the base selected from triethylamine, triethanolamine, diisopropylethylamine, di-n-propylamine or mixtures thereof;

As used herein term "methylating agent" selected from dimethyl sulfate, methyl iodide and dimethyl carbonate.

The first aspect of the present invention provides an improved process for the preparation of lacosamide compound of formula-1, which comprises of O-methylating the (R)-2-acetamido-N-benzyl-3-hydroxypropanamide compound of formula-2

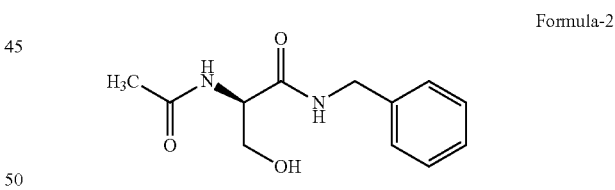

Formula-2 with suitable methylating agent like dimethyl sulfate in presence of a suitable aqueous base in a suitable solvent and in presence of a phase transfer catalyst to provide the lacosamide compound of formula-1.

Wherein the suitable base used is selected from either inorganic or organic bases, preferably inorganic base such as alkali metal hydroxides. And the suitable solvent used is selected from hydrocarbon solvents, ester solvents, polar aprotic solvents, ether solvents, nitrile solvents, chloro solvents, keto solvents or mixtures thereof, preferably hydrocarbon solvents.

In a preferred embodiment, the process for the preparation of lacosamide compound of formula-1 comprises of O-methylating the (R)-2-acetamido-N-benzyl-3-hydroxypropanamide compound of formula-2

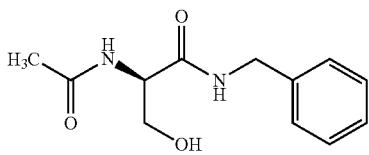
Formula-2

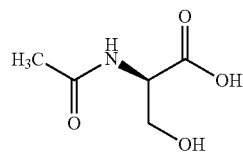
Formula-4 with dimethyl sulfate in presence of aqueous sodium hydroxide and tetrabutylammonium bromide in toluene to provide the lacosamide compound of formula-1.

The second aspect of the present invention provides an improved process for the preparation of lacosamide compound of formula-1, which comprises of O-methylating the (R)-2-acetamido-N-benzyl-3-hydroxypropanamide compound of formula-2

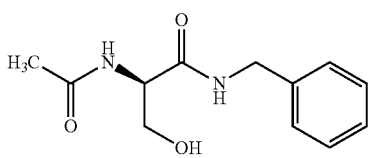
Formula-2 with suitable methylating agent like dimethyl sulfate in presence of a base in a suitable solvent and in the absence of a phase transfer catalyst to provide the lacosamide compound of formula-1.

The base used in the present invention is selected from inorganic or organic bases, preferably alkali metal hydroxide such as sodium hydroxide. And the suitable solvent used is selected from hydrocarbon solvents, ester solvents, polar aprotic solvents, ether solvents, nitrile solvents, chloro solvents, keto solvents or mixtures thereof, preferably hydrocarbon solvents.

The third aspect of the present invention provides an improved process for the preparation of (R)-2-acetamido-N-benzyl-3-hydroxypropanamide compound of formula-2,

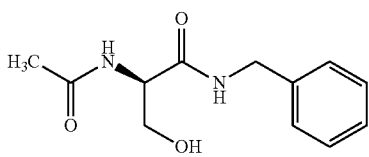
Formula-2 which comprises of
a) Reacting the (R)-2-amino-3-hydroxypropanoic acid compound of formula-3

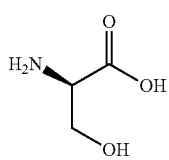
Formula-3 with acetic anhydride in a suitable solvent like acetic acid provides (R)-2-acetamido-3-hydroxypropanoic acid compound of formula-4, b) reacting the compound of formula-4 with benzylamine in presence of a suitable base selected from triethylamine, triethanolamine, di-n-propylamine, diisopropylethylamine and 4-methylmorpholine, preferably 4-methylmorpholine and a activator selected from alkylchloroformate such as isobutyl chloroformate in a suitable solvent selected from ether solvents like tetrahydrofuran or methyl tertiary butyl ether; chloro solvents like methylene chloride or ethylene chloride or mixtures thereof, to provide the compound of formula-2.

The fourth aspect of the present invention provides a process for the purification of (R)-2-acetamido-N-benzyl-3-hydroxypropanamide compound of formula-2, which comprises of the following steps;
(a) Dissolving/suspending the (R)-2-acetamido-N-benzyl-3-hydroxypropanamide compound of formula-2 in a suitable solvent selected from chloro solvents, ether solvents, alcohol solvents, ester solvents, nitrile solvents, keto solvents, hydrocarbon solvents, water or mixtures thereof,
(b) stirring the reaction mixture,
(c) filtering the solid and washing with suitable solvent,
(d) drying the solid to get the pure compound of formula-2.

In a preferred embodiment, the process for the purification of (R)-2-acetamido-N-benzyl-3-hydroxypropanamide compound of formula-2 comprises of the following steps;
(a) Dissolving/suspending the (R)-2-acetamido-N-benzyl-3-hydroxypropanamide compound of formula-2 in a mixture of methylene chloride and methyl tertiary butyl ether,
(b) stirring the reaction mixture for an hour at 25-35° C.,
(c) filtering the precipitated solid and washing with methyl tertiary butyl ether,
(d) drying the solid to get the pure compound of formula-2.

The fifth aspect of the present invention provides a process for the purification of lacosamide compound of formula-1, which comprises of the following steps,
(a) Dissolving/suspending the lacosamide compound of formula-1 in a suitable solvent selected from chloro solvents, nitrile solvents, ether solvents, alcohol solvents, ester solvents, keto solvents, hydrocarbon solvents and water or mixtures thereof,
(b) stirring the reaction mixture,
(c) cooling the reaction mixture and stirring,
(d) filtering the solid and washing with suitable solvent,
(e) drying the solid to get the pure compound of formula-1.

In a preferred embodiment, the process for the purification of lacosamide compound of formula-1 comprises of the following steps;
(a) Suspending the lacosamide compound of formula-1 in ethyl acetate,
(b) stirring the reaction mixture for an hour at 25-35° C.,
(c) cooling the reaction mixture to 0-5° C. and stirring for 1 hour,
(d) filtering the solid and washing with chilled ethyl acetate,
(e) drying the solid to get the pure lacosamide compound of formula-1.

The sixth aspect of the present invention provides a novel process for the preparation of lacosamide compound of formula-1, Formula-1

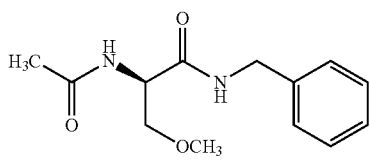

which comprises of the following steps;

a) Treating the (R)-2-amino-3-hydroxypropanoic acid compound of formula-3

Formula-3

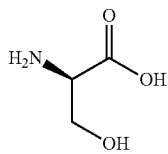

with isobutyl chloroformate in presence of a suitable base selected from inorganic or organic bases in a suitable solvent or mixtures thereof, provides (R)-3-hydroxy-2-(isobutoxycarbonylamino) propanoic acid compound of formula-5, Formula-5

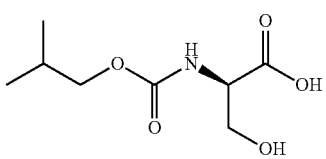

b) O-methylating the compound of formula-5 with suitable methylating agent in presence of a suitable organic or inorganic base or its aqueous solution in a suitable solvent or mixtures thereof and in presence or absence of phase transfer catalyst, provides the (R)-2-(isobutoxycarbonylamino)-3-methoxypropanoic acid compound of formula-6, Formula-6

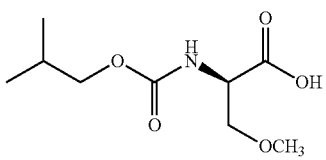

c) reacting the compound of formula-6 with benzylamine in presence of a inorganic or organic base and activator in a suitable solvent or mixture of solvents provides the (R)-isobutyl 1-(benzyl amino)-3-methoxy-1-oxopropan-2-ylcarbamate compound of formula-7, Formula-7

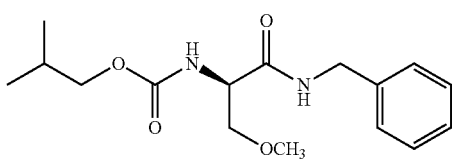

d) treating the compound of formula-7 with suitable acid selected from inorganic or organic acids in a suitable solvent or mixture of solvents to provides the (R)-2-amino-N-benzyl-3-methoxypropanamide compound of formula-8, Formula-8

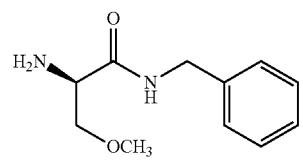

e) reacting the compound of formula-8 with acetic anhydride in a suitable solvent or mixture of solvents provides the lacosamide compound of formula-1.

The seventh aspect of the present invention is to provide an improved process for the preparation of lacosamide compound of formula-1, which comprises of the following steps;

a) Esterifying the (R)-2-amino-3-hydroxypropanoic acid compound of formula-3

Formula-3

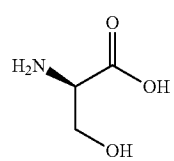

with suitable alcoholic solvent in presence of dry HCl provides the (R)-alkyl-2-amino-3-hydroxypropanoate hydrochloride compound of general formula-9, Formula-9

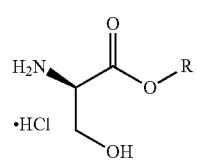

Wherein R refers to alkyl, b) reacting the compound of general formula-9 with benzylamine in a suitable solvent or mixtures thereof provides (R)-2-amino-N-benzyl-3-hydroxypropanamide compound of formula-10, Formula-10

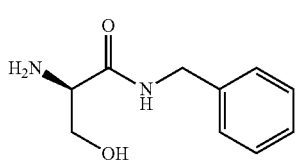

c) reacting the compound of formula-10 with acetic anhydride in a suitable solvent or mixture of solvents provides the (R)-2-acetamido-N-benzyl-3-hydroxypropanamide compound of formula-2,

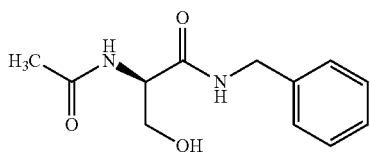
Formula-2

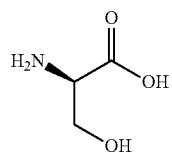
Formula-3 d) O-methylating the compound of formula-2 with suitable methylating agent in presence of a suitable base selected from organic or inorganic base or its aqueous solution in a suitable solvent or mixtures thereof and in presence or absence of phase transfer catalyst provides lacosamide compound of formula-1.

The eighth aspect of the present invention is to provide an improved process for the preparation of lacosamide compound of formula-1, which comprises of the following steps;

a) Reacting the (R)-2-amino-3-hydroxypropanoic acid compound of formula-3

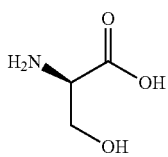
Formula-3 with acetic anhydride in a suitable solvent provides the (R)-2-acetamido-3-hydroxypropanoic acid compound of formula-4,

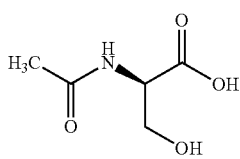
Formula-4 b) O-methylating the compound of formula-4 with suitable methylating agent in presence of a base or its aqueous solution in a suitable solvent and in presence or absence of phase transfer catalyst provides (R)-2-acetamido-3-methoxypropanoic acid compound of formula-11,

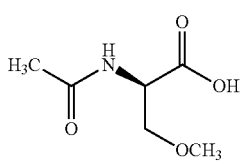
Formula-11 c) reacting the compound of formula-11 with benzylamine in presence of a base and activator in a suitable solvent provides lacosamide compound of formula-1.

The ninth aspect of the present invention is to provide a process for the methylation of (R)-2-amino-3-hydroxypropanoic acid compound of formula-3 without protecting amine functional group, which comprises of treating the compound of formula-3 with a suitable methylating agent in presence of a suitable base in a suitable solvent and in presence or absence of a phase transfer catalyst to provide the (R)-2-amino-3-methoxypropanoic acid compound of formula-12.

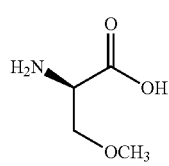
Formula-12

The tenth aspect of the present invention provides an improved process for the preparation of (R)—N-benzyl-2-amino-3-methoxypropionamide compound of formula-8,

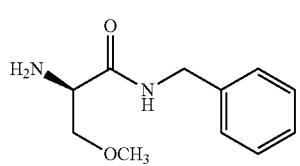
Formula-8 which comprises of deprotection of N-protecting group from (R)—N-benzyl-2-N-(benzyloxycarbonyl)amino-3-methoxypropionamide compound of formula-15,

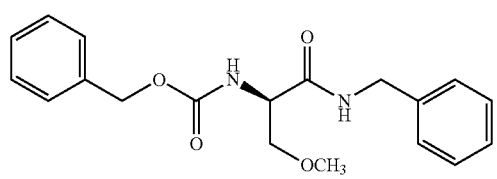
Formula-15 characterized in that the deprotection is carried out in presence of suitable acid selected from hydrochloric acid, sulphuric acid or phosphoric acid to provide the compound of formula-8. The said deprotection is carried out with or without usage of suitable solvents and the solvent is selected from polar solvents, alcohol solvents, chloro solvents and hydrocarbon solvents. The said reaction is carried out at a suitable temperature ranges between 20 to 80° C.

In a preferred embodiment, the process for the preparation of (R)—N-benzyl-2-amino-3-methoxypropionamide compound of formula-8 comprises treating the compound of formula-15 with hydrochloric acid at 40-45° C. and isolating the formula-8 by methods known in the art.

The eleventh aspect of the present invention provides an improved process for the preparation of (R)—N-benzyl-2-N-(benzyloxycarbonyl)amino-3-methoxypropionamide compound of formula-15, Formula-15

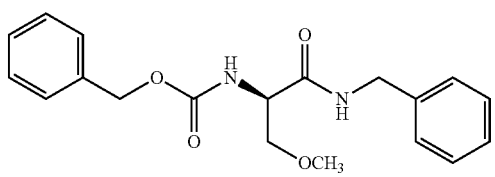

which comprises of reacting (R)—N-benzyl-2-N-(benzyloxycarbonyl)amino-3-hydroxypropionamide compound of formula-14

Formula-14

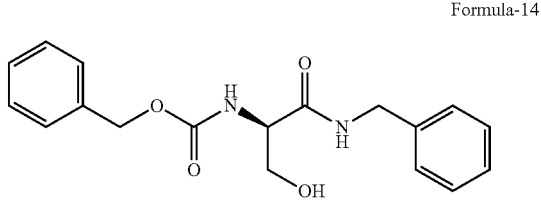 [SMILES: O=C(N[C@H](CO)C(=O)NCc1ccccc1)OCc1ccccc1]

with a suitable methylating agent selected from dimethyl sulphate, methyl iodide or trimethyl phosphate in a presence of a suitable base selected from sodium hydroxide, potassium hydroxide, lithium hydroxide, sodium carbonate, potassium carbonate, sodium methoxide, sodium ethoxide, potassium methoxide, potassium ethoxide, sodium tertiary butoxide, potassium tertiary butoxide or their aqueous solutions and a phase transfer catalyst in a suitable solvent selected from polar solvent, polar aprotic solvent, hydrocarbons or mixtures thereof to provide the (R)—N-benzyl-2-N-(benzyloxycarbonyl) amino-3-methoxypropionamide compound of formula-15.

In a preferred embodiment, the process for the preparation of (R)—N-benzyl-2-N-(benzyloxycarbonyl)amino-3-methoxypropionamide compound of formula-15 comprises of reacting (R)—N-benzyl-2-N-(benzyloxycarbonyl)amino-3-hydroxypropionamide compound of formula-14 with dimethyl sulphate in presence of aqueous sodium hydroxide, tetra butyl ammonium bromide (TBAB) in water to provide the compound of formula-15.

The twelfth aspect of the present invention provides an improved process for the preparation of lacosamide compound of formula-1, which comprises of the following steps, a) Reacting the D-serine compound of formula-3

Formula-3

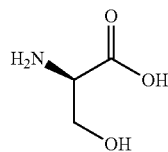

with benzylchloroformate in a suitable alkali metal carbonate or hydroxide bases in a suitable polar solvent to provide the (R)—N-(benzyloxycarbonyl)serine compound of formula-13, Formula-13

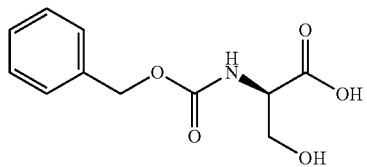

b) reacting the compound of formula-13 with benzylamine in presence of isobutylchloroformate or ethylchloroformate and N-methyl morpholine in a suitable solvent selected from polar aprotic solvent and chloro solvents or mixtures thereof to provide the (R)—N-benzyl-2-N-(benzyloxycarbonyl)amino-3-hydroxypropionamide compound of formula-14, Formula-14

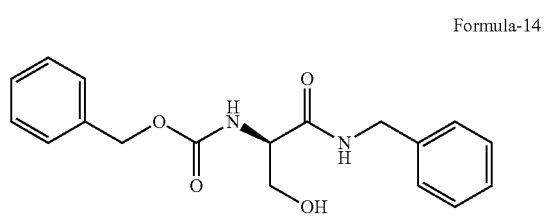 [SMILES: O=C(N[C@H](CO)C(=O)NCc1ccccc1)OCc1ccccc1]

c) methylating the compound of formula-14 by treating with a suitable methylating agent like dimethylsulphate, methyl iodide and trimethylphosphate in a presence of a suitable base selected from sodium hydroxide, potassium hydroxide, lithium hydroxide, sodium bicarbonate, potassium bicarbonate, sodium carbonate, potassium carbonate sodium methoxide, sodium ethoxide, potassium methoxide, potassium ethoxide, sodium tertiary butoxide, potassium tertiary butoxide or their aqueous solutions and a phase transfer catalyst in a suitable solvent selected from polar solvent, polar aprotic solvents, hydrocarbons or mixtures thereof provides (R)—N-benzyl-2-N-(benzyloxycarbonyl)amino-3-methoxypropionamide compound of formula-15, Formula-15

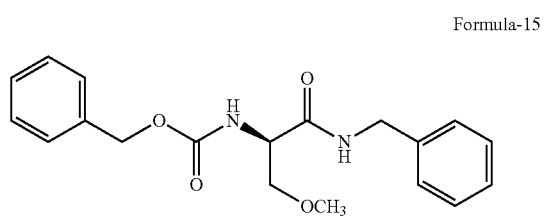 [SMILES: COC[C@@H](NC(=O)OCc1ccccc1)C(=O)NCc1ccccc1]

d) deprotecting the N-protection group from the compound of formula-15 with a suitable acid selected from hydrochloric acid, sulphuric acid or phosphoric acid with or without the usage of solvent selected from alcohol solvents, chloro solvents and hydrocarbon solvents or mixtures thereof to provide the (R)—N-benzyl-2-amino-3-methoxypropionamide compound of formula-8,

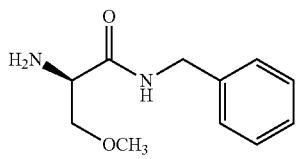

Formula-8 e) reacting the compound of formula-8 with acetic anhydride in a suitable solvent selected from chloro solvents, ester solvent or hydrocarbon solvent to provide the lacosamide compound of formula-1,
f) optionally purifying the lacosamide using a suitable solvent selected from chloro solvents or ester solvent or mixtures thereof provides highly pure lacosamide compound of formula-1.

In a preferred embodiment of the present invention, improved process for the preparation of lacosamide compound of formula-1 comprises of the following steps,
a) Reacting the D-serine compound of formula-3 with benzylchloroformate in presence of sodium bicarbonate in water to provide the (R)—N-(benzyloxycarbonyl)serine compound of formula-13,
b) reacting the compound of formula-13 with benzylamine in presence of isobutylchloroformate and N-methyl morpholine in methylene chloride to provide the (R)—N-benzyl-2-N-(benzyloxycarbonyl)amino-3-hydroxypropionamide compound of formula-14,
c) methylating the compound of formula-14 by treating with dimethylsulphate in presence of aqueous sodium hydroxide, tetra butyl ammonium bromide (TBAB) in water provides (R)—N-benzyl-2-N-(benzyloxycarbonyl)amino-3-methoxy propionamide compound of formula-15,
d) treating the compound of formula-15 with hydrochloric acid to provide the (R)—N-benzyl-2-amino-3-methoxypropionamide compound of formula-8,
e) reacting the compound of formula-8 with acetic anhydride in methylene chloride to provide the lacosamide compound of formula-1,
f) purifying the lacosamide using a ethyl acetate provides highly pure lacosamide compound of formula-1.

The thirteenth aspect of the present invention provides one-pot process for the preparation of lacosamide compound of formula-1, which comprises of
a) Treating the (R)—N-benzyl-2-N-(benzyloxycarbonyl) amino-3-methoxy propionamide compound of formula-15 with a suitable acid selected from hydrochloric acid, sulphuric acid or phosphoric acid or its aqueous solutions,
b) heating the reaction mixture and stirring,
c) quenching the reaction mixture with water and
d) basifying the reaction mixture with suitable aqueous alkali metal hydroxide or alkali metal carbonates/bicarbonate bases,
e) extracting the reaction mixture into suitable chloro solvent, ester solvent or hydrocarbon solvent,
f) cooling the reaction mixture,
g) treating the extracted reaction mixture with acetic anhydride,
h) washing the reaction mixture with aqueous basic solution,
i) distilling off the solvent from the reaction mixture under reduced pressure,
j) crystallizing the obtained crude from ester solvents.

In a preferred embodiment, one-pot process for the preparation of lacosamide compound of formula-1 comprises of a) Treating the (R)—N-benzyl-2-N-(benzyloxycarbonyl) amino-3-methoxy propionamide compound of formula-15 with hydrochloric acid,
b) heating the reaction mixture to 40-45° C. and stirring for 45 minutes,
c) quenching the reaction mixture with water and
d) basifying the reaction mixture aqueous sodium hydroxide solution,
e) extracting the reaction mixture into methylene chloride,
f) cooling the reaction mixture to 0-5° C.,
g) treating the extracted reaction mixture with acetic anhydride,
h) washing the reaction mixture with aqueous sodium bicarbonate followed by water,
i) distilling off methylene chloride from the reaction mixture under reduced pressure,
j) crystallizing the obtained crude from ethyl acetate to provide the lacosamide.

The (R)—N-benzyl-2-amino-3-methoxypropionamide can also be isolated as its organic acid addition salts and is prepared by treating the (R)—N-benzyl-2-amino-3-methoxypropionamide compound of formula-8 with a suitable organic acid selected from oxalic acid, succinic acid, fumaric acid, malonic acid, malic acid, maleic acid, tartaric acid, citric acid, methane sulfonic acid, para toluene sulfonic acid and acetic acid in a suitable solvent to provide the corresponding salt of (R)—N-benzyl-2-amino-3-methoxypropionamide. These salts can be obtained in either crystalline or amorphous form. Thus obtained (R)—N-benzyl-2-amino-3-methoxypropionamide organic acid addition salts are used to prepare highly pure compound of formula-8 and lacosamide compound of formula-1.

The fourteenth aspect of the present invention provides an improved process for the preparation of (R)-2-(t-butoxycarbonylamino)3-methoxypropanoic acid compound of formula-17,

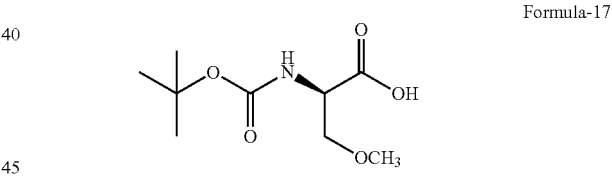

Formula-17 which comprises of O-methylating the N-Boc-D-serine compound of formula-16

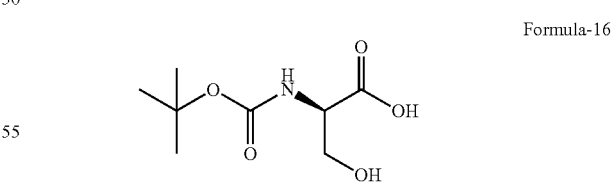

Formula-16 with a suitable methylating agent in the presence of base, in a single phase solvent system without usage of a phase transfer catalyst.

Preferably the suitable methylating agent used is selected from dimethylsulphate or dimethyl carbonate and base is selected from potassium hydroxide, sodium hydroxide, calcium hydroxide and lithium hydroxide etc.

Preferably the solvent used for single phase system is selected from polar solvents like alcohol solvents such as methanol, ethanol, isopropanol and water, most preferably water and the reaction carried out at a temperature of 0-15° C., preferably 5-10° C.

In a preferred embodiment of the present invention, process for the preparation of (R)-2-(t-butoxycarbonylamino)3-methoxypropanoic acid compound of formula-17 comprises of O-methylating the N-Boc-D-serine compound of formula-16 with dimethyl sulfate in presence of sodium hydroxide and water at 5-10° C.

The fifteenth aspect of the present invention-provides an improved process for the preparation of N-Boc-D-serine compound of formula-16,

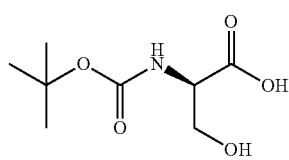

Formula-16 which comprises of protecting the D-serine compound of formula-3

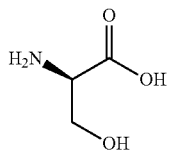

Formula-3 with a suitable N-protecting reagent in presence of a base, in a single phase solvent system without the usage of phase transfer catalyst.

Preferably the N-protecting agent is di-t-butyl dicarbonate (DIBOC) and a base used is selected from potassium hydroxide, sodium hydroxide, calcium hydroxide and lithium hydroxide etc.

Preferably the solvent used for single phase system is selected from polar solvents like alcohol solvents such as methanol, ethanol, isopropanol and water, most preferably water and the reaction carried out at a temperature of 15-30° C., preferably 20-25° C.

In a preferred embodiment of the present invention, the process for the preparation of N-Boc-D-serine compound of formula-16 comprises of protecting the D-serine compound of formula-3 with di-t-butyl dicarbonate (DIBOC) in the presence of sodium hydroxide and water at 20-25° C.

The sixteenth aspect of the present invention provides one-pot process for the preparation of lacosamide compound of formula-1,

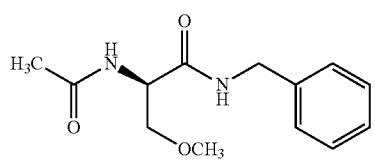

Formula-1 which comprises of reacting the D-serine compound of formula-3 with suitable N-protecting reagent, in the presence of a base in a single solvent system without usage of phase transfer catalyst to provide the N-Boc-D-serine compound of formula-16,

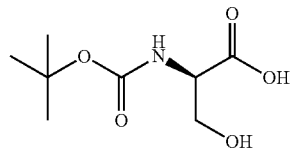

Formula-16 treating the N-Boc-D-serine compound of formula-16 in-situ with suitable methylating agent in the presence of a suitable base, in a single solvent system without usage of phase transfer catalyst to provide ((R)-2-(t-butoxycarbonylarnino)3-methoxypropanoic acid compound of formula-17,

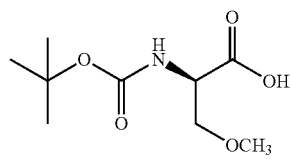

Formula-17 and reacting the compound of formula-17 in-situ with benzylamine in the presence of ethylchloroformate or isobutylchloroformate and N-methyl morpholine in a suitable chloro solvents selected from methylene chloride, chloroform and carbon tetrachloride to provide the (R)-2-tert-butyl-1-(benzylamino)-3-methoxy-1-oxopropan-2-ylcarbonate compound of formula-18,

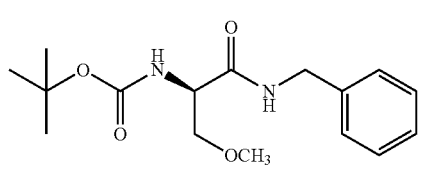

Formula-18 and treating the compound of formula-18 in-situ with a suitable inorganic acid selected from hydrochloric acid, sulphuric acid or phosphoric acid in presence or absence of a solvent to provide the (R)—N-benzyl-2-amino-3-methoxypropionamide compound of formula-8,

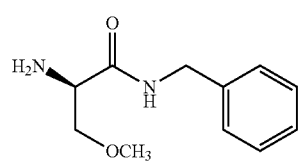

Formula-8 then reacting the compound of formula-8 in-situ with acetic anhydride at a suitable temperature of 15-25° C., preferably 20-25° C. in a suitable chloro solvent selected from methylene chloride, chloroform and carbon tetrachloride to provide the lacosamide compound of formula-1, and optionally purifying the lacosamide using a suitable solvent selected from ester solvents such as ethyl acetate, ethyl butyrate, isobutyl acetate preferably ethyl acetate gives highly pure lacosamide compound of formula-1.

In a preferred embodiment of the present invention, one-pot process for the preparation of lacosamide comprises of protecting the D-serine compound of formula-3 with di-t-butyl dicarbonate in the presence of sodium hydroxide and water at 20-25° C. to provide N-Boc-D-serine compound of formula-3, which on in-situ reaction with dimethyl sulfate in presence of sodium hydroxide and water at 5-10° C. to provide (R)-2-(t-butoxycarbonylamino)3-methoxypropanoic acid compound of formula-4, which on in-situ reaction with benzylamine in the presence of ethylchloroformate and N-methyl morpholine in methylene chloride to provide the (R)-2-tert-butyl-1-(benzylamino)-3-methoxy-1-oxopropan-2-ylcarbonate compound of formula-5, which on in-situ treatment with hydrochloric acid to provide the (R)—N-benzyl-2-amino-3-methoxypropionamide compound of formula-6, which on in-situ treatment with acetic anhydride at 20-25° C. to provide the lacosamide compound of formula-1.

The seventeenth aspect of the present invention provides novel acid addition salts of (R)—N-benzyl-2-amino-3-methoxypropionamide represented by the following structural formula-19,

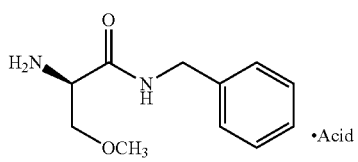

Formula-19 wherein "Acid" is a acid which are capable of forming acid addition salt with (R)—N-benzyl-2-amino-3-methoxypropionamide compound of formula-8 and selected from oxalic acid, succinic acid, fumaric acid, malonic acid, malic acid, maleic acid, tartaric acid, citric acid, methane sulfonic acid, para toluene sulfonic acid, acetic acid, sulfuric acid, phosphoric acid and hydrohalic acid. Novel acid addition salts of the present invention are used to prepare highly pure compound of formula-8 and lacosamide compound of formula-1.

The (R)—N-benzyl-2-amino-3-methoxypropionamide compound of formula-8 prepared as per the prior art processes having very less purity in the range of 90-92% by HPLC. The present inventors surprisingly found that the purity of the (R)—N-benzyl-2-amino-3-methoxypropionamide can be further enhanced up to 96-98%, by forming its acid addition salts and converting back into free base compound of formula-8. Hence it is advantageous to have high purity intermediate compound of formula-8 and its usage in the preparation of highly pure lacosamide compound of formula-1.

Further the present invention provides a process for the preparation of acid addition salt of (R)—N-benzyl-2-amino-3-methoxypropionamide compound of formula-19, which comprises of reacting the compound of formula-8 with a suitable acid as defined above in a suitable solvent selected from alcoholic solvent, ketone solvent and the like, to provide the corresponding salt compound of formula-19.

Further the present invention provides a process for the preparation of highly pure compound of formula-8, which comprises of treating (R)—N-benzyl-2-amino-3-methoxypropionamide with a suitable acid to provide corresponding salt compound of formula-19 and converting the salt compound of formula-19 into highly pure compound of formula-8 by treating it with suitable base in a suitable solvent, wherein the obtained (R)—N-benzyl-2-amino-3-methoxypropionamide is having high purity than the starting (R)—N-benzyl-2-amino-3-methoxypropionamide.

The highly pure compound of formula-8 further converted into highly pure lacosamide by treating with acetic anhydride in a suitable solvent per the process known in the art.

In a preferred embodiment, the present invention provides oxalic acid salt of (R)—N-benzyl-2-amino-3-methoxypropionamide compound of formula-19a and it's used to prepare highly pure lacosamide compound of formula-1 and formula-8.

In a preferred embodiment, the present invention provides a process for the preparation of (R)—N-benzyl-2-amino-3-methoxypropionamide oxalate salt compound of formula-19a, which comprises of the following steps, a) Dissolving the compound of formula-8 in isopropyl alcohol, b) adding a solution of oxalic acid in isopropyl alcohol and stirring, c) cooling the reaction mixture 0-5° C., d) raise the temperature to 10-15° C. and stirring, e) filtering off the solid and washed with isopropyl alcohol, f) drying the obtained solid to get (R)—N-benzyl-2-amino-3-methoxypropionamide oxalate.

The following impurities are generally formed in the preparation of lacosamide.

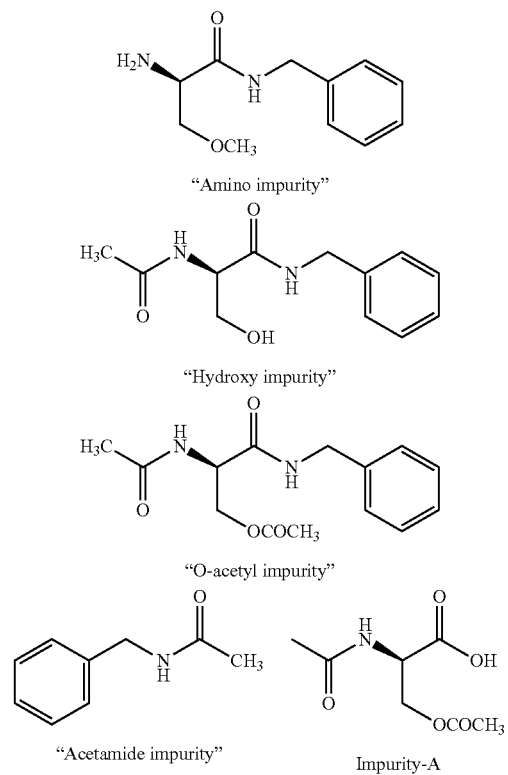

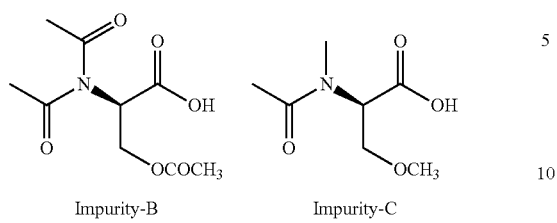
Impurity-B    Impurity-C
The present invention is schematically represented as follows
Scheme-I:
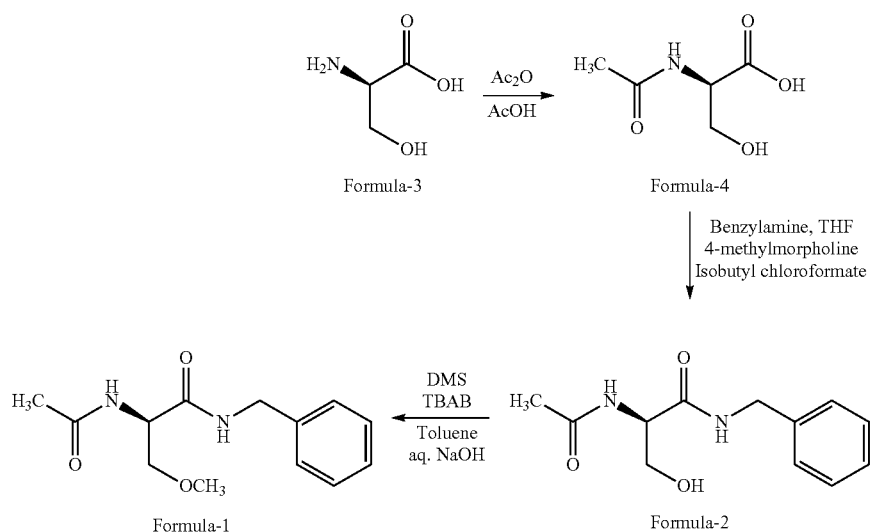
Scheme-II:
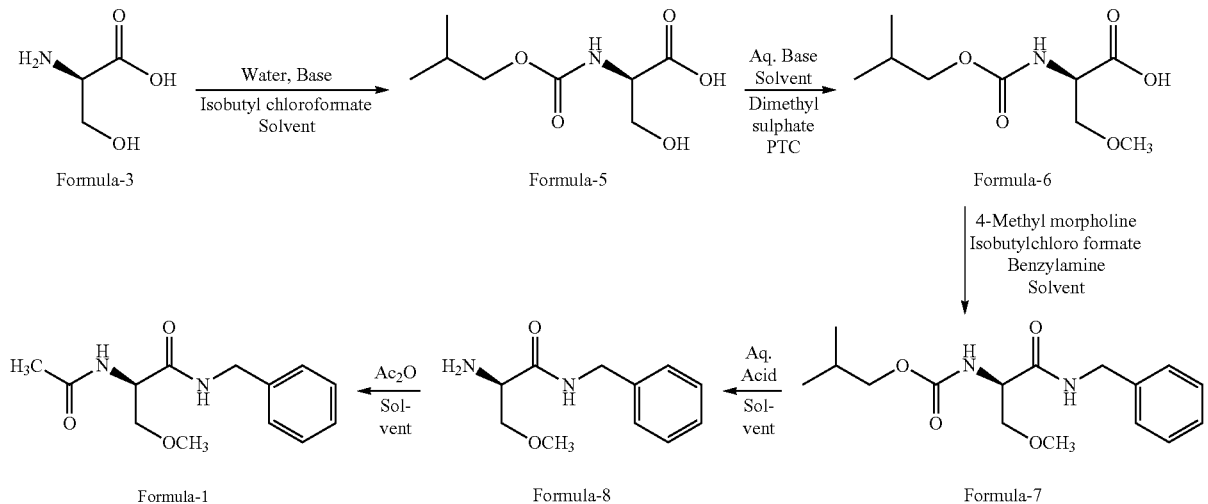

Scheme-III:
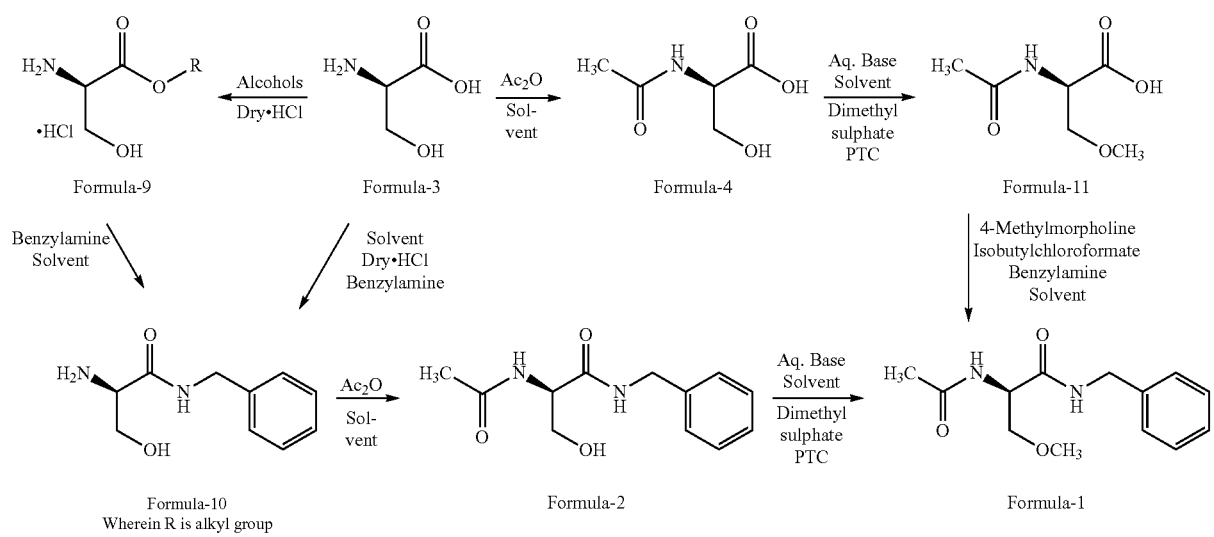
Scheme-IV:
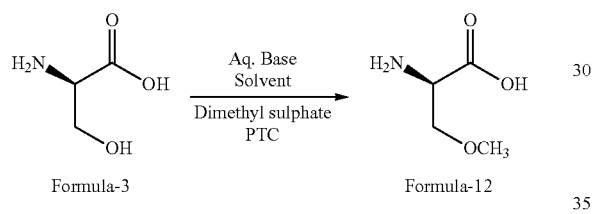
Scheme-V:
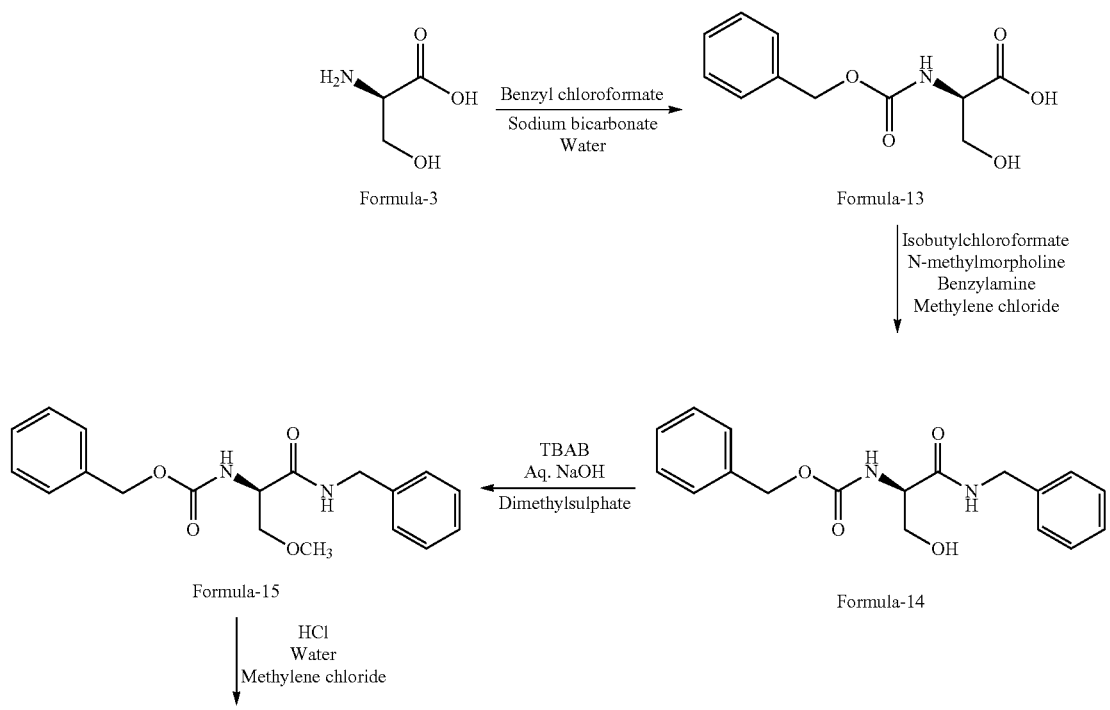

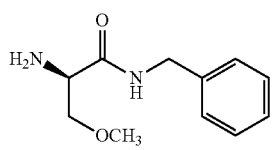 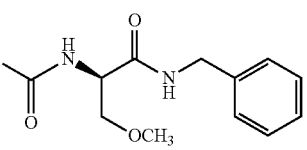

Formula-8 → Formula-1 (Acetic anhydride, Methylene chloride, Ethyl acetate)

The process disclosed in example-2(b) of U.S. Pat. No. 5,773,475 for the preparation of lacosamide was repeated in the laboratory and the obtained solid was analyzed by Powder X-ray diffractogram. Thus obtained PXRD of crystalline lacosamide is represented in FIG. 1.

Further lacosamide obtained as per the present invention is further micronized or milled to get the desired particle size. Milling or micronization may be performed before drying, or after the completion of drying of the product. Techniques that may be used for particle size reduction include, with out limitation, ball, roller and hammer mills, and jet mills.

As used herein the term "pure" refers to the compound having purity greater than 98.00%, preferably greater than 99.00% and more preferably greater than 99.50% by HPLC.

PXRD analysis of lacosamide was carried out using SIEMENS/D-5000 X-Ray diffractometer using Cu, Ka radiation of wavelength 1.54 A° and continuous scan speed of 0.045°/min.

Related substances of the lacosamide and intermediate compounds were analyzed by HPLC using the following conditions:
Apparatus: A liquid chromatograph is equipped with variable wavelength UV-detector. Column: X-bridge $C_{18}$ 150×4.6 mm, 5 μm or equivalent; Flow rate: 1.0 ml/min; Wavelength: 210 nm; Temperature: 25° C.; Injection volume 20 μL; Run time 40 min; Elution: isocratic; and using acetonitrile and buffer in 85:15 v/v ratio as a mobile phase. Buffer is aqueous solution of triethylamine. (or)
Apparatus: A liquid chromatograph is equipped with variable wavelength UV-detector. Column: Symmetry C18 250×4.6 mm, 5 μm or equivalent; Flow rate: 1.0 ml/min; Wavelength: 210 nm; Temperature: 35° C.; Injection volume 10 μL; Run time 40 min; Elution: Gradient; and using buffer and acetonitrile in 90:10 v/v ratio as a mobile phase-A, acetonitrile and water in 60:40 v/v ratio as a mobile phase-B. Buffer is aqueous solution of potassium di hydrogen ortho phosphate (1.36 grams) dissolved in water (1000 ml) and adjusted the pH to 2.0 with dilute ortho phosphoric acid.

The process described in the present invention was demonstrated in examples illustrated below. These examples are provided as illustration only and therefore should not be construed as limitation of the scope of the invention.

EXAMPLES

Example-1

Preparation of Lacosamide Compound of Formula-1

To a solution of (R)-2-acetamido-N-benzyl-3-hydroxypropanamide (15 grams) in toluene (150 ml), tetrabutylammonium bromide (0.82 grams) was added and cooled to 5-1.0° C. Aqueous sodium hydroxide (15 ml) was added to it and stirred for 30 minutes. Dimethyl sulfate (24.27 ml) was added to the reaction mixture slowly and stirred for 30 minutes. Aqueous sodium hydroxide (23.4 ml) was added to the reaction mixture and stirred up to completion the reaction at 5-10° C. The reaction mixture was quenched with water and the aqueous layer was separated. Aqueous layer was acidified with citric acid and extracted into methylene chloride. The methylene chloride layer dried with sodium sulphate and distilled off completely to get the title compound as a solid.

Yield: 5 grams

Example-2

Purification of Lacosamide Compound of Formula-1

Ethyl acetate (25 ml) was added to Lacosamide obtained in example-1 and stirring the reaction mixture for an hour at 25-35° C. The reaction mixture was cooled to 0-5° C. and stirred for an hour. The solid was filtered, washed with ethyl acetate and dried to get high pure compound of formula-1. The PXRD of obtained solid was similar to the PXRD represented in FIG. 1.

Yield: 3.5 grams; Purity by HPLC: 99.58%.

Example-3

Purification of Lacosamide Compound of Formula-1

The title compound was purified in a similar manner to example-2 except that a mixture of ethyl acetate (20 ml) and isopropyl acetate (5 ml) is used in place of ethyl acetate.

Yield: 3.6 grams

Purity by HPLC: 99.61%

Example-4

Preparation of (R)-2-acetamido-N-benzyl-3-hydroxypropanamide of formula-2

4-methylmorpholine (7.3 ml) followed by isobutylchloroformate (12.35 ml) was added to a suspension of (R)-2-acetamido-3-hydroxypropanoic acid (7 grams) in tetrahydrofuran (147 ml) at −78 to −75° C., benzylamine (10.4 ml) was added to it and the reaction mixture temperature was raised to 30-35° C. then stirred for 30 minutes. The reaction mixture was filtered and the filtrate was distilled off under reduced pressure. The obtained residue was dissolved in methylene chloride (35 ml) and washed with aqueous hydrochloric acid followed by sodium carbonate and then with water. The solvent from the methylene chloride layer was distilled off completely under reduced pressure to get the title compound.

Yield: 8 grams

Purity by HPLC: 88.50%

Example-5

Purification of (R)-2-acetamido-N-benzyl-3-hydroxypropanamide compound of formula-2

The (R)-2-acetamido-N-benzyl-3-hydroxypropanamide compound of formula-2 obtained in example-4 was dissolved in a mixture of methylene chloride (8 ml) and methyl tertiarybutyl ether (40 ml). The reaction mixture was stirred for an hour at 25-35° C. The obtained solid was filtered, washed with methyl tertiary butyl ether and then dried to the get the pure title compound.
Yield: 5 grams
Purity by HPLC: 98.20%

Example-6

Purification of (R)-2-acetamido-N-benzyl-3-hydroxypropanamide compound of formula-2

The compound of formula-2 (4 grams) obtained in example-4 was dissolved in a mixture of chloroform (4 ml) and methyl tertiarybutyl ether (20 ml). The reaction mixture was stirred for an hour at 25-35° C. The obtained solid was filtered, washed with methyl tertiary butyl ether and then dried to the get the pure title compound.
Yield: 2.6 grams
Purity by HPLC: 98.50%

Example-7

Preparation of (R)-2-acetamido-3-hydroxypropanoic acid formula-4

Acetic anhydride (10.79 ml) was added to a suspension of D-serine (10 grams) in acetic acid (150 ml) and stirred at 25-35° C. After completion of the reaction, acetic acid was removed by distillation followed by co-distillation with tetrahydrofuran. Isopropyl alcohol (30 ml) and methyltertiarybutylether (60 ml) was added to the obtained residue and stirred for 30 minutes. The obtained solid was filtered off and then solvent from the filtrate was distilled off completely under reduced pressure to get the title compound.
Yield: 15 grams

Example-8

Preparation of (R)-3-hydroxy-2-(isobutoxycarbonylamino)propanoic acid compound of formula-5

Isobutylchloroformate (19.51 grams) in tetrahydrofuran was added to mixture of (R)-2-amino-3-hydroxypropanoic acid compound of formula-2 (10 grams), water (100 ml), sodium carbonate (27.25 grams) at 0-5° C. and stirred for 1 hour. The reaction mixture was quenched with water and then ethyl acetate was added to it. The aqueous layer was acidified with hydrochloric acid. The reaction mixture extracted into methylene chloride, dried the methylene chloride layer with sodium sulphate and then distilled off the solvent under reduced pressure get the title compound.
Yield: 10 grams.

Example-9

Preparation of (R)-2-(isobutoxycarbonylamino)-3-methoxypropanoic acid compound of formula-6

To a solution of (R)-3-hydroxy-2-(isobutoxycarbonylamino) propanoic acid compound of formula-5 (10 grams) in toluene (100 ml), teterabutylammonium bromide (0.63 grams) was added and cooled to 5-10° C. Aqueous sodium hydroxide (9.5 ml) was added to it and stirred for 30 minutes. Dimethyl sulfate (18.6 ml) was added to the reaction mixture slowly and stirred for 6 hours at 5-10° C. The reaction mixture was quenched with water and the aqueous layer was separated. Aqueous layer was acidified with citric acid and extracted into methylene chloride. The methylene chloride layer was dried with sodium sulphate and distilled off completely to get the title compound.
Yield: 10 grams.

Example-10

Preparation of (R)-methyl 2-amino-3-hydroxypropanoate hydrochloride compound of formula-9a Dry hydrochloric acid gas was passed into methanol (625 ml) at 0-5° C. and then (R)-2-amino-3-hydroxypropanoic acid compound of formula-3 (50 grams) was added to the reaction mixture. The reaction mixture was heated to 60-65° C. and stirred for 20 hours. The reaction mixture was distilled off under reduced pressure. Methyl tertiary butyl ether (234 ml) was added to the obtained residue at reflux temperature and stirred for 1 hour. Then the reaction mixture was cooled to 40° C. The obtained solid was filtered, washed with methyl tertiary butyl ether and then dried to get the title compound.
Yield: 70 grams

Example-11

Preparation of (R)-2-amino-N-benzyl-3-hydroxypropanamide compound of formula-10

The (R)-methyl 2-amino-3-hydroxypropanoate hydrochloride compound of formula-9a was dissolved in methanol (625 ml) and then cooled to 10-15° C. Benzyl amine (77.5 grams) was added to the reaction mixture at 10-15° C., then heated the reaction mixture to 60-65° C. and stirred for 18 hours. After completion of the reaction, the reaction mixture was distilled off under reduced pressure. Chloroform was added to the obtained residue and the obtained solid was separated out by filtration. The filtrate was washed with water and the organic layer was distilled off completely under reduced pressure to get the title compound.
Yield: 70 grams.

Example-12

Preparation of (R)-2-amino-N-benzyl-3-hydroxypropanamide compound of formula-10

Dry hydrochloric acid gas was passed into methanol (125 ml) at 0-5° C. and then (R)-2-amino-3-hydroxypropanoic acid compound of formula-3 (10 grams) was added to the reaction mixture. The reaction mixture was heated to 60-65°

C. and stirred for 20 hours. Then the reaction mixture was cooled to 20° C. and benzylamine (40.8 grams) was added to the reaction mixture. Then heated the reaction mixture to 60-65° C. and stirred for 20 hours. After completion of the reaction, the reaction mixture was distilled off under reduced pressure. Chloroform was added to the obtained residue and the solid was separated out by filtration. The filtrate was washed with water and the organic layer was distilled off completely under reduced pressure and then gets the title compound.

Yield: 9 grams.

Example-13

Preparation of (R)-2-acetamido-N-benzyl-3-hydroxypropanamide of compound of formula-2

Acetic anhydride (4 grams) was added to the solution of (R)-2-amino-N-benzyl-3-hydroxypropanamide compound of formula-10 (6 grams) in dichloromethane (60 ml) at 10-15° C. The reaction mixture was stirred for 3 hours and reaction mixture quenched with water. Both the organic and aqueous layers were separated. The organic layer was washed with aqueous sodium bicarbonate solution followed by water. The organic layer was distilled off completely under reduced pressure to get the title compound.

Yield: 6.6 grams.

Example-14

Preparation of (R)-2-acetamido-3-hydroxypropanoic acid of compound of formula-4

Acetic anhydride (23.4 ml) was added to the suspension of (R)-2-amino-3-hydroxypropanoic acid compound of formula-3 (20 grams) in acetic acid (300 ml) and stirred for 24 hours at 30-35° C. After completion of the reaction, acetic acid was removed by distillation followed by co-distillation with tetrahydrofuran. Isopropyl alcohol (60 ml) and methyl-tertiarybutylether (120 ml) was added to the obtained residue and stirred for 30 minutes. The obtained solid was filtered off and then solvent from the filtrate was distilled off completely under reduced pressure to get the title compound.

Yield: 28 grams.

Example-15

Preparation of (R)-2-acetamido-3-methoxypropanoic acid compound of formula-11

To a solution of (R)-2-acetamido-3-hydroxypropanoic acid compound of formula-4 (13.0 grams) in toluene (65 ml), tetrabutylammonium bromide (1.06 grams) was added and cooled to 5-10° C. Aqueous sodium hydroxide (17.7 ml) was added to it and stirred for 30 minutes. Dimethyl sulfate (33.5 ml) was added to the reaction mixture slowly and stirred for 30 minutes. Aqueous sodium hydroxide (32.0 ml) was added to the reaction mixture and stirred up to completion the reaction at 5-10° C. The reaction mixture was quenched with water and the aqueous layer was separated. Aqueous layer was acidified with citric acid and extracted into methylene chloride. The methylene chloride layer dried with sodium sulphate and distilled off completely to get the title compound as a solid.

Yield: 5.2 grams.

Example-16

Preparation of Lacosamide Compound of Formula-1

To a solution of (R)-2-acetamido-N-benzyl-3-hydroxypropanamide compound of formula-2 (9 grams) in methylene chloride (150 ml), teterabutylammonium bromide (0.491 grams) was added and cooled to 5-10° C. Aqueous sodium hydroxide (7.5 ml) was added to it and stirred for 30 minutes. Dimethyl sulfate (9.78 ml) was added to the reaction mixture slowly and stirred for 30 minutes. Aqueous sodium hydroxide (7.5 ml) was added to the reaction mixture and stirred up to completion the reaction at 5-10° C. The reaction mixture was quenched with water and the aqueous layer was separated. Aqueous layer was acidified with citric acid and extracted into methylene chloride. The methylene chloride layer dried with sodium sulphate and distilled off completely to get the title compound as a solid.

Yield: 5 grams

Example-17

Preparation of Lacosamide Compound of Formula-1

4-methylmorpholine (1.1 ml) followed by isobutylchloroformate (1.3 ml) was added to a suspension of (R)-2-acetamido-3-methoxypropanoic acid compound of formula-11 (1.0 gram) in tetrahydrofuran (20 ml) at −78 to −75° C., benzylamine (1.35 ml) was added to it and the reaction mixture temperature was raised to 30-35° C. then stirred for 30 minutes. The reaction mixture was filtered and the filtrate was distilled off under reduced pressure. Water was added to the obtained residue and washed with toluene. Aqueous layer was extracted with chloroform and this chloroform layer was distilled off completely under reduced pressure to get the title compound.

Yield: 0.8 grams.

Example-18

Preparation of (R)—N-(benzyloxycarbonyl)serine of formula 13

Sodium bicarbonate (240 g) was added to a mixture of D-serine (100 g) and water (800 ml) at 0-5° C. Benzylchloroformate (50% solution in toluene)(480 ml) was added to the reaction mixture and stirred for 10 hours at 0-5° C. The organic and aqueous layers were separated and washed the aqueous layer with toluene. Aqueous layer pH was adjusted to 1.5 with hydrochloric acid and extract the reaction mixture in to ethyl acetate. Distilled off the solvent from the extracted reaction mixture under reduced pressure to get the title compound.

Yield: 195 grams

Example-19

Preparation of (R)—N-(benzyloxycarbonyl)serine of formula 13

Sodium bicarbonate (60 g) was added to a mixture of D-serine (25 g) and water (375 ml) at 15-20° C. Benzylchloroformate (50% solution in toluene)(120 ml) was added slowly to the reaction mixture and stirred for 10 hours at 15-20° C. Filtered the reaction mixture and the filtrate was taken. The organic and aqueous layers were separated and washed the aqueous layer with methylene chloride. Aqueous layer pH was adjusted to 1.5 with hydrochloric acid. Stirred the reaction mixture for 90 minutes. Filtered the solid and washed with water. Dried the material to get the title compound.

Yield: 48 grams

Example-20

Preparation of (R)—N-benzyl-2-N-(benzyloxycarbonyl)amino-3-hydroxypropionamide compound of formula-14

Isobutylchloroformate (17 ml) was added to the pre cooled mixture of (R)—N-(benzyloxycarbonyl)serine (25 g) and methylene chloride (312 ml) at below −65 to −70° C. and stirred for 15 minutes. N-Methylmorpholine (16.2 ml) was added at −70° C. and stirred for 30 min. Benzylamine (14.3 ml) was added to the reaction mixture and stirred for 5 hours at −70° C. The reaction mixture temperature was raised to 20-25° C. and filtered the undissolved salts then washed with methylene chloride. The solvent from the reaction mixture was distilled off completely under reduced pressure at 40-45° C. to get the title compound.

Yield: 30 grams

Example-21

Preparation of (R)—N-benzyl-2-N-(benzyloxycarbonyl)amino-3-hydroxypropionamide compound of formula-14

Ethylchloroformate (25 g) was slowly added to the pre cooled mixture of (R)—N-(benzyloxycarbonyl)serine (50 g) and methylene chloride (500 ml) at below −30 to −20° C. and stirred for 15 minutes. N-Methylmorpholine (23.2 g) was slowly added at −30° C. and stirred for 30 min. Benzylamine (25 g) was added to the reaction mixture and stirred for 90 minutes −30° C. The reaction mixture temperature was raised to 20-25° C. and stirred for 90 minutes. The solvent from the reaction mixture was distilled off completely under reduced pressure at 40-45° C. Cooled the obtained compound to 20-25° C. and added aqueous sodium hydroxide solution and toluene. Stirred the reaction mixture for 90 minutes. Filtered the precipitated solid and washed with water. Dried the material to get the title compound.

Yield: 61 grams

Example-22

Preparation of (R)—N-benzyl-2-N-(benzyloxycarbonyl)amino-3-methoxy propionamide compound of formula-15

Aqueous sodium hydroxide (3 ml, 20%) was added to a mixture of (R)—N-benzyl-2-N-(benzyloxycarbonyl)amino-3-hydroxy propionamide (5 g) in water (50 ml) and n-Tetrabutylammoniumbromide (TBAB) (0.2 g) at 0-5° C. Dimethylsulphate (5.7 ml) and 50% sodium hydroxide solution (9.6 ml) were simultaneously added to the reaction mixture at 0-5° C. and stirred for 3 hours. The solid obtained was filtered off, washed with water and then dried at 30-35° C. to get the title compound.

Yield: 3 grams

Example-23

Preparation of (R)—N-benzyl-2-N-(benzyloxycarbonyl)amino-3-methoxy propionamide compound of formula-15

The title compound is prepared in a similar manner to example-22 except that cyclohexane used in place of water.

Yield: 2.8 grams

Example-24

Preparation of (R)—N-benzyl-2-N-(benzyloxycarbonyl)amino-3-methoxy propionamide compound of formula-15

To the −10 to −5° C. pre cooled aqueous sodium hydroxide solution (15.2 g dissolved in 50 ml of water) added methyl tertiary butyl ether (125 ml), tetrabutylammonium bromide (5 g) and (R)—N-benzyl-2-N-(benzyloxycarbonyl)amino-3-hydroxy propionamide (25 g) at −10 to −5° C. Dimethylsulphate (74 ml) was slowly added to the reaction mixture at 0-5° C. and stirred for 12 hours at same temperatures. The solid obtained was filtered off, washed with methyl tertiary butyl ether. Water was added to the obtained compound and stirred for 45 minutes at 20-30° C. Filtered the solid and dried at 60-65° C. to get the title compound.

Yield: 19 grams

Example-25

Preparation of (R)—N-benzyl-2-amino-3-methoxypropionamide compound of formula-8

A mixture of 2-N-(benzyloxycarbonyl)amino-3-methoxy propionamide (15 grams) and concentrated hydrochloric acid (150 ml) was heated to 40-45° C. and stirred for 45 mins. The reaction mixture was cooled to 0-5° C. Water (75 ml) was added to the reaction mixture and basified with aqueous sodium hydroxide solution. The reaction mixture is extracted into methylene chloride. The methylene chloride layer containing (R)—N-benzyl-2-amino-3-methoxypropionamide compound of formula-8 used directly in next step.

Example-26

Preparation of Lacosamide Compound of Formula-1

Acetic anhydride (3.57 g) was added to methylene chloride layer containing (R)—N-benzyl-2-amino-3-methoxypropionamide (150 ml) obtained as per example-25 at 0-5° C. and stirred for an hour. The reaction mixture was washed with sodium bicarbonate solution followed by water. The reaction mixture was dried over sodiumsulphate and the solvent was distilled off under reduced pressure. Ethyl acetate (30 ml) was added and distilled off completely. Ethyl acetate (60 ml) was added to the residue and heated to reflux temperature. The reaction mixture was cooled to 45-50° C. and stirred for 4 hours. The reaction mixture was further cooled to 0-5° and stirred for 45 mins. The solid obtained was filtered off, washed with ethyl acetate and dried to get the title compound.

Yield: 6 grams

Example-27

Preparation of (R)—N-benzyl-2-amino-3-methoxypropionamide compound of formula-8

A mixture of 2-N-(benzyloxycarbonyl)amino-3-methoxy propionamide (60 grams) and concentrated hydrochloric acid (360 ml) was heated to 40-45° C. and stirred for 8 hours. The reaction mixture was cooled to 20-25° C. Washed the reaction mixture with methylene chloride and basified with aqueous sodium hydroxide solution (45 grams in 125 ml of water). The compound from the reaction mixture is extracted into methylene chloride. The methylene chloride layer containing (R)—N-benzyl-2-amino-3-methoxypropionamide compound of formula-8 used directly in next step.

Example-28

Preparation of Lacosamide Compound of Formula-1

Acetic anhydride (18 grams) was added to methylene chloride layer containing (R)—N-benzyl-2-amino-3-methoxypropionamide (270 ml) obtained as per example-27 at 20-25° C. and stirred for an hour. The reaction mixture was washed with sodium carbonate solution followed by water. The reaction mixture was dried over sodium sulphate and the solvent was distilled off under reduced pressure. Ethyl acetate (60 ml) was added and distilled off completely. Ethyl acetate (180 ml) was added to the residue and heated to reflux temperature and stirred for 30 minutes. Filtered the reaction mixture through hyflow bed. The reaction mixture was cooled to 55-60° C. and stirred for 4 hours. The reaction mixture was further cooled to 0-5° and stirred for 45 mins. The solid obtained was filtered off, washed with ethyl acetate and dried to get the title compound.

Yield: 31 grams

Example-29

One Pot Process for Lacosamide

A mixture of 2-N-(benzyloxycarbonyl)amino-3-methoxy propionamide (15 grams) and concentrated hydrochloric acid (150 ml) was heated to 40-45° C. and stirred for 45 mins. The reaction mixture was cooled to 0-5° C. Water (75 ml) was added to the reaction mixture and basified with aqueous sodium hydroxide solution. The reaction mixture is extracted into methylene chloride. Acetic anhydride (3.57 g) was added to reaction mixture at 0-5° C. and stirred for an hour. The reaction mixture was washed with sodiumbicarbonate solution followed by water. The reaction mixture was dried over sodiumsulphate and the solvent was distilled off under reduced pressure. Ethyl acetate (30 ml) was added and distilled off completely. Ethylacetate (60 ml) was added to the residue and heated to reflux temperature. The reaction mixture was cooled to 45-50° C. and stirred for 4 hours. The reaction mixture was further cooled to 0-5° and stirred for 45 mins. The solid obtained was filtered off, washed with ethyl acetate and dried to get the title compound.

Yield: 5.6 grams

Example-30

Preparation of N-Boc-D-serine of formula 16

Di-tert.butyldicarbonate (124.5 grams) was added to solution of D-serine (50 grams) in aqueous sodium hydroxide (38.5 g of NaOH in 250 ml of water) at 20-25° C. and stirred for 10 hours at 20-25° C. The reaction mixture containing N-Boc-D-serine has been used directly to next stage with out any purification.

Example-31

Preparation of (R)-2-(tert-butoxycarbonylamino)-3-methoxy propionic acid compound of formula-17

Sodium hydroxide (19 g) was added to a reaction mixture containing N-Boc-D-serine (430 ml) obtained in example-30 at 0-5° C. and stirred for 30 mins. Dimethylsulphate (340 ml) and sodium hydroxide solution (153 g in 152 ml of water) was added reaction mixture slowly over 4 hours at 5-10° C. and then stirred for 10 hrs. The pH of the reaction mass was acidified with dilute hydrochloric acid at 0-5° C. Methylene chloride (100 ml) was added to the reaction mixture and the layers get separated. Aqueous layer was extracted with methylene chloride and the methylene chloride layer containing the title compound was directly used for the next stage without any purification.

Example-32

Preparation of (R)-2-tert-butyl 1-(benzylamino)-3-methoxy-1-oxopropan-2-yl carbonate compound of formula-18

Ethylchoroformate (49.3 g) followed by N-methylmorpholine (46 g) was added to a pre-cooled reaction mass of (R)-2-(tert-butoxycarbonylamino)-3-methoxy propionic acid (280 ml) obtained in example-31 at −10 to −15° C. and stirred for 15 min at −15° C. Benzylamine (49 g) was added to the reaction mixture slowly at −10 to −15° C. and stirred for 1.5 hours. Reaction temperature was raised to 20-25° C. and stirred for 1.5 hours. The reaction mixture was washed with dilute hydrochloric acid (100 ml), and further the organic layer was washed with sodium bicarbonate solution followed by washed with water. The reaction mixture containing title compound was directly used for next stage without any isolation and purification.

Example-33

Preparation of (R)—N-benzyl-2-amino-3-methoxypropionamide compound of formula-8

Concentrated hydrochloric acid (175 ml) was added to a reaction mixture containing (R)-2-tert-butyl 1-(benzylamino)-3-methoxy-1-oxopropan-2-yl carbonate (280 ml) obtained in example-32 at 0-5° C. and stirred for 3 hrs. The organic and aqueous layers were separated. Aqueous layer was basified with sodium hydroxide and the reaction mixture extracted into methylene chloride. The methylene chloride layer containing the title compound used directly in the next step without any further isolation or purification.

Example-34

Preparation of Lacosamide Compound of Formula-1

Acetic anhydride (48.5 g) was added to methylene chloride layer containing (R)—N-benzyl-2-amino-3-methoxypropionamide (390 ml) obtained in example-33 at 20-25° C. and stirred for an hour. The reaction mixture was washed with sodium carbonate solution followed by water, and the solvent from the reaction mixture was distilled off under atmospheric pressure. Ethyl acetate (50 ml) was added to the residue and distilled off it completely. Ethyl acetate (250 ml) was added to the obtained residue and heated to 75-80° C., stirred for 30 minutes and filtered through hyflow. The filtrate was cooled to 55-60° C. and stirred for 4 hours. The reaction mixture was further cooled to 0-5° and stirred for 1 hr. The solid obtained was filtered off and washed with ethyl acetate. Ethyl acetate was added to the wet solid and heated to 75-80° C. and stirred for 45 min at 75-80° C. The reaction mixture was cooled to 20-25° C. and stirred for 1.30 hrs. The solid obtained was filtered off, and washed with ethyl acetate and dried to get the title compound.

Yield: 65 grams

Purity by HPLC: 99.86%; 0-actyl impurity: 0.05%; acetamide impurity: 0.05%; amino impurity: Not detected; hydroxyl impurity: 0.01%

Example-35

Preparation of (R)—N-benzyl-2-amino-3-methoxypropionamide oxalate compound of formula-19a A solution of oxalic acid (2.1 grams) in isopropyl alcohol (5 ml) was added to a solution of (R)—N-benzyl-2-amino-3-methoxypropionamide having purity of 91.8% (5 grams) in isopropyl alcohol (10 ml) at 25-32° C. and stirred for 15 minutes. The reaction mixture was cooled to 0-5° and stirred for 30 min. Then the reaction mixture was stirred for 30 minutes at 10-15° C. The solid obtained was filtered, washed with isopropyl alcohol and dried to get the title compound.

Yield: 2.5 grams
Purity by HPLC: 97%

Example-36

Preparation of Highly Pure (R)—N-benzyl-2-amino-3-methoxy propionamide compound of formula-8

Water (10 ml) was added to (R)—N-benzyl-2-amino-3-methoxy propionamide oxalate compound of formula-19a (1 gram) and the reaction mixture was basified with sodium hydroxide solution. Extracted the reaction with methylene chloride and distilled off the methylene chloride layer to get the title compound.

Yield: 0.6 grams
Purity by HPLC: 96.8%

Example-37

Purification of Lacosamide Compound of Formula-1

Ethyl acetate (25 ml) was added to Lacosamide (5 g) and stirring the reaction mixture for an hour at 25-35° C. The reaction mixture was heated to 75-80° C. and stirred for 45 minutes. Cooled the reaction mixture to 20-25° C. The solid was filtered, washed with ethyl acetate and dried to get high pure compound of formula-1. The PXRD of obtained solid was similar to the PXRD represented in FIG. 1.

Yield: 3.5 grams; Purity by HPLC: 99.99%.
Particle Size Distribution: D (0.1): 3.80 μm; D (0.5): 12.05 μm; D (0.9): 121.69 μm; D[4,3]: 42.37 μm.

We claim:

1. A process for the preparation of lacosamide compound of Formula-1,

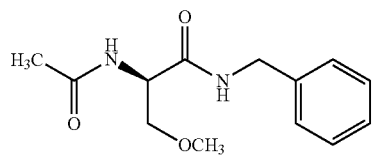

Formula-1 the process comprising:
a) reacting a compound of Formula-10

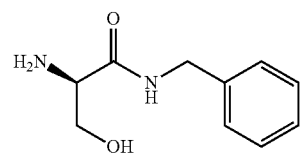

Formula-10 with acetic anhydride in a solvent or mixture of solvents to produce a compound of Formula-2; and

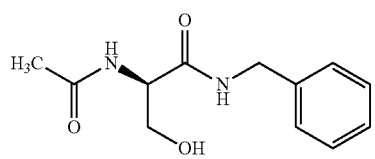

Formula-2 b) O-methylating the compound of Formula-2 with a methylating agent in presence of a base selected from an organic base or inorganic base or its aqueous solution in a solvent or solvent mixture and in presence or absence of phase transfer catalyst to produce lacosamide compound of Formula-1, wherein the organic base is selected from triethylamine, triethanolamine, diisopropylethylamine or di-n-propylamine, or a mixture of the foregoing; and the inorganic base is selected from an alkali metal hydroxide, an alkali metal carbonate, an alkali metal bicarbonate or an alkali metal alkoxide, or a mixture of the foregoing.

2. The process according to claim 1, wherein the methylating agent is selected from dimethylsulfate, methyl iodide and trimethylphosphate.

3. The process of claim 1, wherein the compound of Formula-10

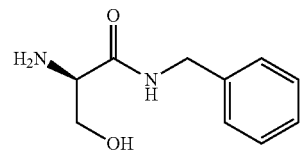

Formula-10 is prepared by the process comprising:
a) esterifying a compound of Formula-3

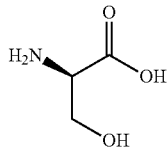

Formula-3 with an alcoholic solvent in presence of dry HCl to produce a compound of Formula-9

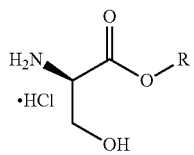

Formula-9 wherein R is $C_{1-6}$ alkyl; and
b) reacting the compound of Formula-9 with benzylamine in a suitable solvent or mixture of solvents to produce compound of Formula-10.

4. The process of claim 1, further comprising:
a) suspending the lacosamide compound of Formula-1 in ethyl acetate, thereby forming a mixture;
b) stirring the mixture for an hour at 25-35° C.;
c) cooling the mixture to 0-5° C. and stirring for an hour, thereby forming a solid;
d) filtering the solid and washing with chilled ethyl acetate; and
e) drying the solid to get lacosamide compound of Formula-1 having a purity of greater than 99.50% by high-performance liquid chromatography (HPLC).

5. The process of claim 1, wherein step (b) comprises O-methylating the compound of Formula-2 with dimethyl sulfate in presence of aqueous sodium hydroxide solution and tetrabutylammonium bromide in toluene to provide the lacosamide compound of Formula-1.

6. The process of claim 1, wherein step a) further comprises:
(i) dissolving or suspending the compound of Formula-2 in a mixture of methylene chloride and methyl tertiary butyl ether to form a reaction mixture;
(ii) stirring the reaction mixture for an hour at 25-35° C.;
(iii) filtering the precipitated solid from step (ii) and washing with methyl tertiary butyl ether; and
(iv) drying the solid from step (iii) to get pure compound of Formula-2.

7. The process according to claim 1, wherein step b) is carried out in absence of the phase transfer catalyst.

8. The process according to claim 1, wherein step b) is carried out at a temperature of from 5° C. to 10° C.

* * * * *